(12) United States Patent
Behkish et al.

(10) Patent No.: US 10,351,486 B2
(45) Date of Patent: Jul. 16, 2019

(54) MULTIPHASE SEPARATOR AND METHODS OF USE THEREOF FOR PRODUCING HYDROCARBONS FROM OXYGENATES AND OLEFINS

(71) Applicant: ExxonMobil Research and Engineering Company, Annandale, NJ (US)

(72) Inventors: Arsam Behkish, Flemington, NJ (US); Michael F. Raterman, Doylestown, PA (US); Surya Bhaskara Reddy Karri, Naperville, IL (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/343,670

(22) Filed: Nov. 4, 2016

(65) Prior Publication Data

US 2017/0137342 A1    May 18, 2017

Related U.S. Application Data

(60) Provisional application No. 62/256,806, filed on Nov. 18, 2015.

(51) Int. Cl.
| | |
|---|---|
| *C07C 1/20* | (2006.01) |
| *B01J 8/08* | (2006.01) |
| *B01J 19/24* | (2006.01) |
| *B01J 8/00* | (2006.01) |
| *C10G 3/00* | (2006.01) |
| *C10G 11/16* | (2006.01) |
| *B01J 8/12* | (2006.01) |

(52) U.S. Cl.
CPC .............. *C07C 1/20* (2013.01); *B01J 8/005* (2013.01); *B01J 8/006* (2013.01); *B01J 8/008* (2013.01); *B01J 8/08* (2013.01); *B01J 8/085* (2013.01); *B01J 8/12* (2013.01); *B01J 19/24* (2013.01); *C10G 3/54* (2013.01); *C10G 11/16* (2013.01); *B01J 2219/24* (2013.01); *Y02P 30/20* (2015.11)

(58) Field of Classification Search
CPC ................................................ C07C 1/20–247
See application file for complete search history.

(56) References Cited

U.S. PATENT DOCUMENTS

| | | | |
|---|---|---|---|
| 2,394,814 A | 2/1946 | Snuggs | |
| 2,443,190 A | 6/1948 | Krebs | |
| 2,554,426 A | 5/1951 | Strunk et al. | |
| 4,414,100 A * | 11/1983 | Krug | C10G 11/18 208/153 |
| 5,318,692 A * | 6/1994 | Eberly, Jr. | C10G 11/05 208/113 |
| 7,988,756 B2 | 8/2011 | Fujiyama et al. | |
| 8,070,846 B2 | 12/2011 | Fujiyama et al. | |
| 8,083,824 B2 | 12/2011 | Fujiyama et al. | |

(Continued)

OTHER PUBLICATIONS

International Search Report and Written Opinion PCT/US2016/060518 dated Feb. 20, 2017.

*Primary Examiner* — Philip Y Louie
*Assistant Examiner* — Alyssa L Cepluch
(74) *Attorney, Agent, or Firm* — Liza Negron

(57) ABSTRACT

Multiphase separators, processes and systems for converting an oxygenate and/or olefin feedstock to a hydrocarbon product are described herein.

19 Claims, 7 Drawing Sheets

(56) References Cited

U.S. PATENT DOCUMENTS

| | | |
|---|---|---|
| 8,313,548 B2 | 11/2012 | Fujiyama et al. |
| 2006/0049082 A1 | 3/2006 | Niccum et al. |
| 2010/0197879 A1 | 8/2010 | De Broqueville et al. |
| 2013/0225393 A1* | 8/2013 | Chewter ................. B01J 29/90 502/6 |

* cited by examiner

1

MULTIPHASE SEPARATOR AND METHODS OF USE THEREOF FOR PRODUCING HYDROCARBONS FROM OXYGENATES AND OLEFINS

CROSS-REFERENCE TO RELATED APPLICATIONS

This application claims priority to U.S. Provisional Application Ser. No. 62/256,806 filed on Nov. 18, 2015, herein incorporated by reference in its entirety.

FIELD

The present invention relates to devices and processes for multiphase separation of process fluid from solids, such as catalyst particles, during processes, such as conversion of oxygenates and/or olefins to hydrocarbons.

BACKGROUND

Processes where reactants are contacted with solid materials, such as catalyst particles, to produce single phase or mixed phase (e.g., gas and liquid) products are commonly used throughout the chemical industry. For example, lower oxygenates such as methanol and dimethyl ether (DME) may be contacted with a molecular sieve catalyst (e.g., a zeolite) and undergo a conversion reaction to produce hydrocarbons. Such methanol conversion processes are known and have become of great interest because they offer an attractive way of producing liquid hydrocarbon fuels, especially gasoline, from sources which are not petrochemical feeds. In particular, they provide a way by which methanol and DME can be converted to gasoline boiling components, olefins and aromatics in good yields. Olefins and aromatics are valuable chemical products and can serve as feeds for the production of numerous important chemicals and polymers. Additionally, olefins may be contacted with a molecular sieve catalyst and be oligomerized to a hydrocarbon product, such as a distillate. Because of the limited supply of competitive petroleum feeds, the opportunities to produce low cost olefins from petroleum feeds are limited. However, methanol may be readily obtained from coal by gasification to synthesis gas and conversion of the synthesis gas to methanol by well-established industrial processes. As an alternative, the methanol may be obtained from natural gas or biomass by other conventional processes.

Deactivation of the catalyst during such processes is a major issue. Typically, the catalyst undergoes a regeneration process to restore its activity. However, some of the catalyst activity may not be restored during regeneration causing irreversible catalyst deactivation, which leads to a shorter cycle life of the catalyst as well as reduced product yield. While utilizing a moving catalyst bed reactor may reduce irreversible catalyst deactivation and provide a longer catalyst cycle life and higher product yield, stripping of the process fluid from the solid catalyst is critical in achieving such benefits. U.S. Pat. Nos. 8,313,548; 8,083,824; 8,070,846; and 7,988,756 describe processes and devices for gas-solid separation of gas phase products from solid catalyst particles. However, processes, such as the methanol and olefin conversion processes described above, may have single phase or mixed phase (e.g., gas and liquid) reactants and products; thus, requiring separation of gases and liquids from solids (e.g., catalyst particles). Therefore, there is a need to provide systems and processes that can provide multiphase separation of process fluid (i.e., gases and liquids) from solids, such as catalyst particles.

SUMMARY

It has been found that multiphase separation of process fluid from solids can be achieved with a separator comprising at least one inlet chamber for introducing a stripping fluid; at least one stripping chamber, which defines perforations therein; and at least one collection chamber; wherein the at least one stripping chamber is generally disposed between the at least one inlet chamber and the at least one collection chamber and at least a portion of the perforations are in fluid communication with the at least one inlet chamber and the at least one collection chamber such that the stripping fluid enters the at least one inlet chamber and flows through the perforations into the at least one stripping chamber and into the at least one collection chamber.

Thus, in one aspect, embodiments of the invention provide a multiphase separator for separating a process fluid from a catalyst comprising: at least one inlet chamber comprising at least one inlet for introducing a stripping fluid; at least one stripping chamber having a top inlet and a bottom outlet, wherein the at least one stripping chamber defines perforations therein, and wherein the top inlet has a diameter greater than the bottom outlet diameter; at least one collection chamber comprising at least one outlet; and wherein the at least one stripping chamber is generally disposed between the at least one inlet chamber and the at least one collection chamber and at least a portion of the perforations are in fluid communication with the at least one inlet chamber and the at least one collection chamber such that the stripping fluid enters the at least one inlet chamber and flows through the perforations into the at least one stripping chamber and into the at least one collection chamber.

In still another aspect, embodiments of the invention provide a reaction system for converting a feedstock to a hydrocarbon product comprising at least one moving bed reactor unit comprising: a reaction vessel comprising at least one feedstock inlet in fluid connection with the reaction vessel; at least one catalyst feed inlet in fluid connection with the reaction vessel; at least one reaction zone; a stripping zone in fluid connection with the reaction zone, wherein the stripping zone comprises the multiphase separator as described herein; and at least one stripped catalyst outlet in fluid connection with the reaction vessel.

In still another aspect, embodiments of the invention provide a process for converting a feedstock to a hydrocarbon product comprising: feeding the feedstock and a catalyst to a reaction zone of at least one moving bed reactor, wherein the feedstock and the catalyst travel through the at least one moving bed reactor under conditions to produce a mixture comprising converted hydrocarbon product, unconverted feedstock, and spent catalyst; passing the mixture to a stripping zone in the at least one moving bed reactor; and separating the mixture in the stripping zone, wherein the separating comprises: collecting the mixture in at least one stripping chamber having a top inlet and a bottom outlet, wherein the at least one stripping chamber defines perforations therein and the top inlet has a diameter greater than a diameter of the bottom outlet, and wherein the at least one stripping chamber is generally disposed between at least one inlet chamber and at least one collection chamber; introducing a stripping fluid into the at least one inlet chamber, wherein the stripping fluid flows into the at least one stripping chamber through the perforations whereby at least a portion of the converted hydrocarbon product and the unconverted feedstock are stripped from the spent catalyst; passing at least a portion of the converted hydrocarbon product and the unconverted feedstock stripped from the spent catalyst through the perforations into the at least one collection chamber; and passing the stripped catalyst through the bottom outlet of the at least one stripping chamber.

In still another aspect, embodiments of the invention provide a process for separating a process fluid from a catalyst comprising: feeding the catalyst and the process fluid into at least one stripping chamber having a top inlet and a bottom outlet, wherein the at least one stripping chamber defines perforations therein and the top inlet has a diameter greater than the bottom outlet diameter, and wherein the at least one stripping chamber is generally disposed between at least one inlet chamber and at least one collection chamber; introducing a stripping fluid into the inlet chamber, wherein the stripping fluid flows into the at least one stripping chamber through the perforations whereby at least a portion of the process fluid is stripped from the catalyst; passing at least a portion of the process fluid stripped from the catalyst through the perforations into the at least one collection chamber; and passing the stripped catalyst through the bottom outlet of the at least one stripping chamber.

Other embodiments, including particular aspects of the embodiments summarized above, will be evident from the detailed description that follows.

DETAILED DESCRIPTION OF THE EMBODIMENTS

Figure 1:
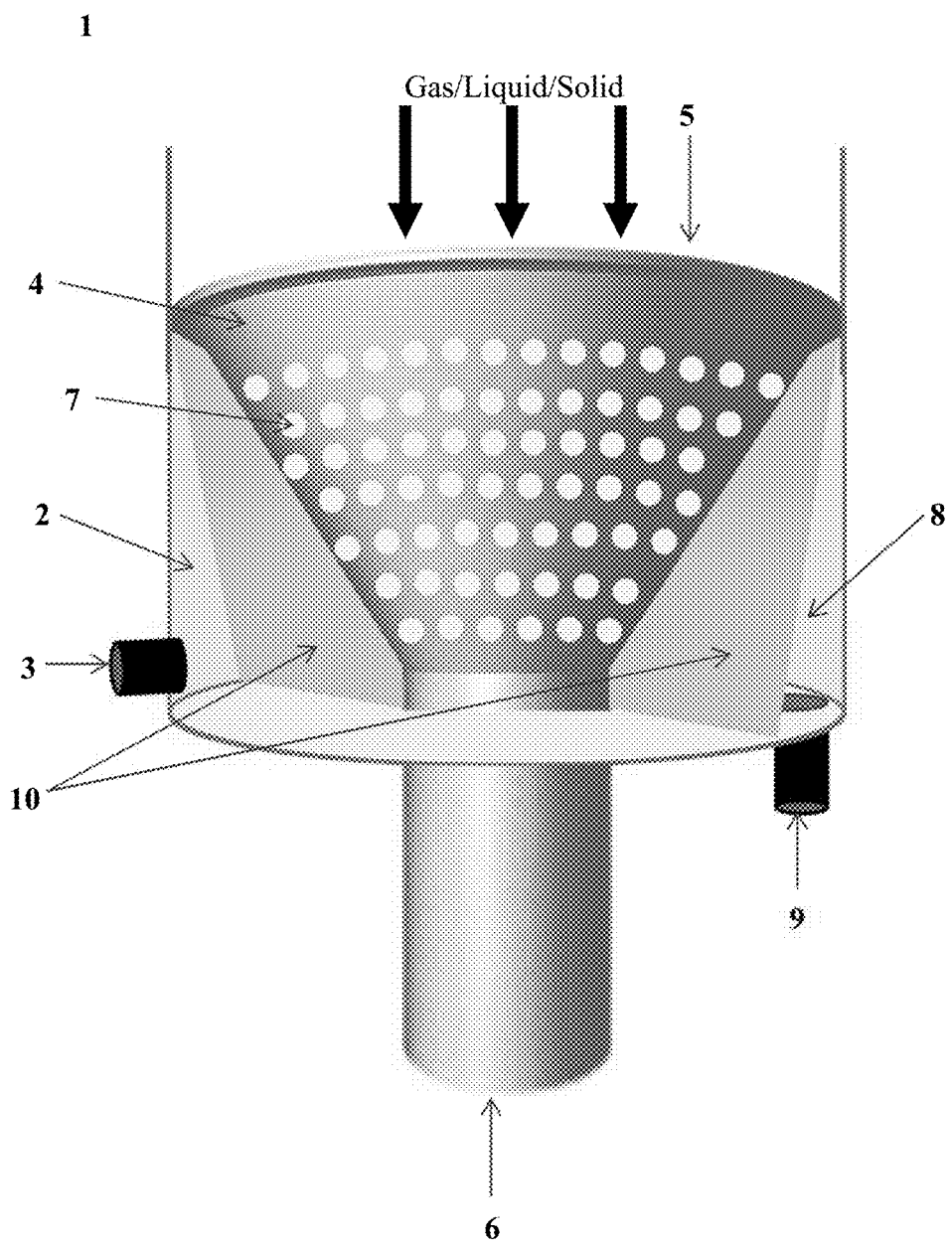
FIG. 1 illustrates an embodiment of a multiphase separator 1.

In various aspects of the invention, multiphase separators and reaction systems and process using the multiphase separators are provided.

I. Definitions

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

As used herein, the term "about" in reference to a value or range of values can mean plus or minus 10% of the value(s)/range. For example, the phrase "about 0.5" includes plus or minus 10% of 0.5, or from 0.45 to 0.55. Additionally or alternatively, the term "about" can encompass any value that can be rounded to a significant digit. Although, in the example of "about 0.5", the significant digit rounding works out to approximately the same range, namely from 0.45 to just under 0.55, these two definitions are not always coterminous.

As used herein, the term "mixed phase" refers to two phases, e.g., liquid and gas, liquid and solid, gas and solid, etc., as opposed to the term "single phase," which refers to one phase.

As used herein, the term "multiphase" refers to two or more phases, particularly three phases, e.g., liquid, gas and solid.

As used herein, the term "diameter" refers to an average diameter of circular cross-sections and an average of the largest cross-sectional distance for non-circular cross-sections.

As used herein, the term "reactor" refers to any vessel(s) in which a chemical reaction occurs. Reactor includes both distinct reactors as well as reaction zones within a single reactor apparatus. In other words and as is common, a single reactor may have multiple reaction zones. Where the description refers to a first and second reactor, the person of ordinary skill in the art will readily recognize such reference includes a single reactor having first and second reaction zones. Likewise, a first reactor effluent and a second reactor effluent will be recognized to include the effluent from the first reaction zone and the second reaction zone of a single reactor, respectively.

As used herein, the term "moving bed reactor" refers to a reactor where a particulate material comprising a catalyst material travels through the reactor and is removed from the reactor. Typically the catalyst material enters at one end of the reactor and flows out the opposite end of the reactor. The moving bed reactor may be a cylindrical vessel or a spherical vessel.

As used herein the phrase "at least a portion of" means >0 to 100 wt % of the process stream or composition to which the phrase refers. The phrase "at least a portion of" refers to an amount from about 0.1 wt % to about 100 wt %, e.g., from about 0.1 wt % to about 99 wt %, from about 0.1 wt % to about 98 wt %, from about 0.1 wt % to about 95 wt %, from about 0.1 wt % to about 90 wt %, from about 0.1 wt % to about 85 wt %, from about 0.1 wt % to about 80 wt %, from about 0.1 wt % to about 75 wt %, from about 0.1 wt % to about 70 wt %, from about 0.1 wt % to about 60 wt %, from about 0.1 wt % to about 50 wt %, from about 0.1 wt % to about 40 wt %, from about 0.1 wt % to about 30 wt %, from about 0.1 wt % to about 25 wt %, from about 0.1 wt % to about 20 wt %, from about 0.1 wt % to about 10 wt %, from about 0.1 wt % to about 5.0 wt %, from about 0.1 wt % to about 2.0 wt %, from about 0.1 wt % to about 1.0 wt %, from about 1.0 wt % to about 100 wt %, from about 1.0 wt % to about 99 wt %, from about 1.0 wt % to about 98 wt %, from about 1.0 wt % to about 95 wt %, from about 1.0 wt % to about 90 wt %, from about 1.0 wt % to about 85 wt %, from about 1.0 wt % to about 80 wt %, from about 1.0 wt % to about 75 wt %, from about 1.0 wt % to about 70 wt %, from about 1.0 wt % to about 60 wt %, from about 1.0 wt % to about 50 wt %, from about 1.0 wt % to about 40 wt %, from about 1.0 wt % to about 30 wt %, from about 1.0 wt % to about 25 wt %, from about 1.0 wt % to about 20 wt %, from about 1.0 wt % to about 10 wt %, from about 1.0 wt % to about 5.0 wt %, from about 1.0 wt % to about 2.0 wt %, from about 2.0 wt % to about 100 wt %, from about 2.0 wt % to about 99 wt %, from about 2.0 wt % to about 98 wt %, from about 2.0 wt % to about 95 wt %, from about 2.0 wt % to about 90 wt %, from about 2.0 wt % to about 85 wt %, from about 2.0 wt % to about 80 wt %, from about 2.0 wt % to about 75 wt %, from about 2.0 wt % to about 70 wt %, from about 2.0 wt % to about 60 wt %, from about 2.0 wt % to about 50 wt %, from about 2.0 wt % to about 40 wt %, from about 2.0 wt % to about 30 wt %, from about 2.0 wt % to about 25 wt %, from about 2.0 wt % to about 20 wt %, from about 2.0 wt % to about 10 wt %, from about 2.0 wt % to about 5.0 wt %, from about 5.0 wt % to about 100 wt %, from about 5.0 wt % to about 99 wt %, from about 5.0 wt % to about 98 wt %, from about 5.0 wt % to about 95 wt %, from about 5.0 wt % to about 90 wt %, from about 5.0 wt % to about 85 wt %, from about 5.0 wt % to about 80 wt %, from about 5.0 wt % to about 75 wt %, from about 5.0 wt % to about 70 wt %, from about 5.0 wt % to about 60 wt %, from about 5.0 wt % to about 50 wt %, from about 5.0 wt % to about 40 wt %, from about 5.0 wt % to about 30 wt %, from about 5.0 wt % to about 25 wt %, from about 5.0 wt % to about 20 wt %, from about 5.0 wt % to about 10 wt %, from about 10 wt % to about 100 wt %, from about 10 wt % to about 99 wt %, from about 10 wt % to about 98 wt %, from about 10 wt % to about 95 wt %, from about 10 wt % to about 90 wt %, from about 10 wt % to about 85 wt %, from about 10 wt % to about 80 wt %, from about 10 wt % to about 75 wt %, from about 10 wt % to about 70 wt %, from about 10 wt % to about 60 wt %, from about 10 wt % to about 50 wt %, from about 10 wt % to about 40 wt %, from about 10 wt % to about 30 wt %, from about 10 wt % to about 25 wt %, from about 10 wt % to about 20 wt %, from about 20 wt % to about 100 wt %, from about 20 wt % to about 99 wt %, from about 20 wt % to about 98 wt %, from about 20 wt % to about 95 wt %, from about 20 wt % to about 90 wt %, from about 20 wt % to about 85 wt %, from about 20 wt % to about 80 wt %, from about 20 wt % to about 75 wt %, from about 20 wt % to about 70 wt %, from about 20 wt % to about 60 wt %, from about 20 wt % to about 50 wt %, from about 20 wt % to about 40 wt %, from about 20 wt % to about 30 wt %, from about 20 wt % to about 25 wt %, from about 25 wt % to about 100 wt %, from about 25 wt % to about 99 wt %, from about 25 wt % to about 98 wt %, from about 25 wt % to about 95 wt %, from about 25 wt % to about 90 wt %, from about 25 wt % to about 85 wt %, from about 25 wt % to about 80 wt %, from about 25 wt % to about 75 wt %, from about 25 wt % to about 70 wt %, from about 25 wt % to about 60 wt %, from about 25 wt % to about 50 wt %, from about 25 wt % to about 40 wt %, from about 25 wt % to about 30 wt %, from about 30 wt % to about 100 wt %, from about 30 wt % to about 99 wt %, from about 30 wt % to about 98 wt %, from about 30 wt % to about 95 wt %, from about 30 wt % to about 90 wt %, from about 30 wt % to about 85 wt %, from about 30 wt % to about 80 wt %, from about 30 wt % to about 75 wt %, from about 30 wt % to about 70 wt %, from about 30 wt % to about 60 wt %, from about 30 wt % to about 50 wt %, from about 30 wt % to about 40 wt %, from about 40 wt % to about 100 wt %, from about 40 wt % to about 99 wt %, from about 40 wt % to about 98 wt %, from about 40 wt % to about 95 wt %, from about 40 wt % to about 90 wt %, from about 40 wt % to about 85 wt %, from about 40 wt % to about 80 wt %, from about 40 wt % to about 75 wt %, from about 40 wt % to about 70 wt %, from about 40 wt % to about 60 wt %, from about 40 wt % to about 50 wt %, from about 50 wt % to about 100 wt %, from about 50 wt % to about 99 wt %, from about 50 wt % to about 98 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 60 wt %, from about 60 wt % to about 100 wt %, from about 60 wt % to about 99 wt %, from about 60 wt % to about 98 wt %, from about 60 wt % to about 95 wt %, from about 60 wt % to about 90 wt %, from about 60 wt % to about 85 wt %, from about 60 wt % to about 80 wt %, from about 60 wt % to about 75 wt %, from about 60 wt % to about 70 wt %, from about 70 wt % to about 100 wt %, from about 70 wt % to about 99 wt %, from about 70 wt % to about 98 wt %, from about 70 wt % to about 95 wt %, from about 70 wt % to about 90 wt %, from about 70 wt % to about 85 wt %, from about 70 wt % to about 80 wt %, from about 70 wt % to about 75 wt %, from about 75 wt % to about 100 wt %, from about 75 wt % to about 99 wt %, from about 75 wt % to about 98 wt %, from about 75 wt % to about 95 wt %, from about 75 wt % to about 90 wt %, from about 75 wt % to about 85 wt %, from about 75 wt % to about 80 wt %, from about 80 wt % to about 100 wt %, from about 80 wt % to about 99 wt %, from about 80 wt % to about 98 wt %, from about 80 wt % to about 95 wt %, from about 80 wt % to about 90 wt %, from about 80 wt % to about 85 wt %, from about 85 wt % to about 100 wt %, from about 85 wt % to about 99 wt %, from about 85 wt % to about 98 wt %, from about 85 wt % to about 95 wt %, from about 85 wt % to about 90 wt %, from about 90 wt % to about 100 wt %, from about 90 wt % to about 99 wt %, from about 90 wt % to about 98 wt %, from about 90 wt % to about 95 wt %, from about 95 wt % to about 100 wt %, from about 95 wt % to about 99 wt %, from about 95 wt % to about 98 wt %, from about 98 wt % to about 100 wt %, from about 98 wt % to about 99 wt %, or from about 99 wt % to about 100 wt %.

As used herein, the term "aromatic" refers to unsaturated cyclic hydrocarbons having 4 to 25 carbon atoms, particularly from 8 to 20 carbon atoms, for example from 4 to 12 carbon atoms. Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms, such as, but not limited to, nitrogen, oxygen, and/or sulfur. Exemplary aromatics with one or more heteroatom include, but are not limited to furan, benzofuran, pyrrole, indole, thiophene, benzothiophene, imidazole, purine, pyrazole, pyridine, quinoline, pyrazine, pyrimidine, indazole, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, the term "olefin" refers to an unsaturated hydrocarbon chain length of from 2 to 30 carbon atoms, particularly from 2 to 12 carbon atoms, particularly from 2 to 9 carbon atoms, particularly from 2 to 8 carbon atoms, particularly from 2 to 6 carbon atoms, particularly from 2 to 4 carbons atoms, containing at least one carbon-to-carbon double bond, e.g., ethylene, propylenes, butylenes, pentylenes, hexylenes, octylenes, decylenes and isomers thereof, preferably ethylene, propylenes, butylenes pentylenes, hexylenes, octylenes, and isomers thereof. The olefin may be straight-chain or branched-chain. As used herein, the term $C_{2+}$ olefin refers to an olefin comprising at least 2 carbon atoms, particularly 2 to 12 carbon atoms, particularly 2 to 9 hydrocarbons, particularly 2 to 8 hydrocarbons. Other non-limiting examples of olefins can include unsaturated monomers, diolefins having 2 to 18 carbon atoms, conjugated or nonconjugated dienes, polyenes, vinyl monomers, and cyclic olefins. "Olefin" is intended to embrace all structural isomeric forms of olefins. As used herein, the term "light olefin" refers to olefins having 2 to 4 carbon atoms (i.e., ethylene, propylenes, and butenes).

As used herein, the term "paraffin" refers to a saturated hydrocarbon chain of 1 to about 25 carbon atoms in length, such as, but not limited to methane, ethane, propane and butane. The paraffin may be straight-chain or branched-chain. "Paraffin" is intended to embrace all structural isomeric forms of paraffins. As used herein, the term "light paraffin" refers to paraffins having 1 to 4 carbon atoms (i.e., methane, ethane, propane and butane).

As used herein, the term "oxygenate" refers to oxygen-containing compounds having from 1 to 50 carbon atoms, particularly from 1 to 20 carbon atoms, particularly from 1 to 10 carbon atoms, particularly from 1 to 4 carbon atoms. Exemplary oxygenates include alcohols, ethers, carbonyl compounds, e.g., aldehydes, ketones and carboxylic acids, and mixtures thereof. Particular non-limiting examples of oxygenates include methanol, ethanol, dimethyl ether, diethyl ether, methylethyl ether, di-isopropyl ether, dimethyl carbonate, dimethyl ketone, formaldehyde, acetic acid, and the like, and combinations thereof.

As used herein, the term "alcohol" refers to a hydroxyl group (—OH) bound to a carbon atom (e.g., an alkyl). Alcohols include monohydric, dihydric, and polyhydric alcohols. Monohydric alcohols, also known as mono-alcohols include one hydroxyl group, such as but not limited to aliphatic, alicyclic, aromatic, heterocyclic, or polycyclic alcohols. Aliphatic alcohols include paraffinic and olefinic alcohols. Examples of monhydric alcohols include, but are not limited to methanol, ethanol, propanol, isopropanol, butanol, isobutanol, n-butanol, tert-butanol, pentanol, hexanol and mixtures thereof. As used herein, the term "butanol" encompasses n-butanol, isobutanol and tert-butanol. As used herein, the term "propanol" encompasses 1-propanol and isopropanol. Dihydric alcohols, also known as diols or di-alcohols, have two hydroxyl groups. Examples of dihydric alcohols include, but are not limited to ethylene glycol, diethylene glycol, catechol, 1,2-cyclohexanediol, 1,3-propanediol, 2,3-butanediol, 1,2-butanediol, 1,4-butanediol, and glycerol. Polyhydric alcohols, also known as polyols, include three or more hydroxyl groups. Examples of polyhydric alcohols include, but are not limited to trimethylolpropane, glycerol, erythritol, pentaerythritol, trimethylolbenzene or trishydroxyethyl isocyanurate. The alcohol may be straight or branched. "Alcohol" is intended to embrace all structural isomeric forms of an alcohol. Additionally or alternatively, the alcohol may be independently substituted with a $C_1$-$C_8$-alkyl. For example, butanol may be substituted with a methyl group, such as, but not limited to 2-methyl-1-butanol and 3-methyl-2-butanol.

As used herein, the term "$C_2$-$C_{22}$ hydrocarbons product" refers to a composition comprising $C_2$-$C_{22}$ hydrocarbons and/or having a boiling point range of about −155° F. to about 710° F.

II. Multiphase Separator

In a first embodiment, as shown in FIG. 1, a multiphase separator 1 for separating a process fluid from solid particles is provided.

A. Inlet Chamber

The multiphase separator 1 may comprise at least one inlet chamber 2 comprising at least one inlet 3 (e.g., one, two, three, four, five, or six inlets, etc.) for introducing a stripping fluid. The at least one inlet chamber 2 may comprise multiple inlet chambers 2, e.g., two inlet chambers 2, three inlet chambers 2, four inlet chambers 2, five inlet chambers 2, six inlet chambers 2, seven inlet chambers 2, eight inlet chambers 2, nine inlet chambers 2, ten inlet chambers 2, etc.

B. Process Fluid

The process fluid may comprise gaseous and/or liquid products and/or unreacted feed.

C. Solid Particles

Typically, the solid particles comprise catalyst particles including fresh, regenerated and/or spent catalyst. Additionally or alternatively the solid particles may further comprise an inert material.

D. Stripping Chamber

Additionally or alternatively, the multiphase separator 1 may further comprise at least one stripping chamber 4 for collecting the process fluid and the solid particles (e.g., catalyst). The at least one stripping chamber 4 has a top inlet 5 and a bottom outlet 6, wherein the top inlet 5 and the bottom outlet 6 may have substantially the same diameter, the top inlet 5 may have a diameter greater than the bottom outlet 6 diameter, or the top inlet 5 may have a diameter less than the bottom outlet 6 diameter. Particularly, the top inlet 5 may have a diameter greater than the bottom outlet 6 diameter. Exemplary diameters of the top inlet 5 include, but are not limited to about 30 cm to about 1200 cm, particularly about 300 cm to about 700 cm. The top inlet 5 and the bottom outlet 6 may each independently have a substantially circular cross-section, a substantially rectangular cross-section, a substantially square cross-section, a substantially elliptical cross-section, particularly a substantially circular cross-section. Additionally or alternatively, the at least one stripping chamber 4 may generally have a conical shape, a wedge shape (also known as a chisel transition) or a frustoconical shape.

Additionally or alternatively, the at least one stripping chamber 4 may define perforations 7 therein whereby the stripping fluid may enter the at least one stripping chamber 4 via the perforations 7, so that at least a portion of the process fluid may be stripped from the solid particles (e.g., catalyst), and the stripped process fluid and the stripping fluid may exit the at least one stripping chamber 4 via the perforations 7. The perforations 7 may be any suitable configuration and/or size having a diameter which is small enough so as to not allow the solid particles from passing through the perforations 7, but large enough to allow a sufficient flow of the stripping fluid into the at least one stripping chamber 4 and a sufficient flow of stripped process fluid to exit the at least one stripping chamber 4. For example, the perforations 7 may have a substantially circular cross-section, a substantially rectangular cross-section, a substantially square cross-section, a substantially elliptical cross-section, or be in the form of slits or slots. The at least one stripping chamber may be formed from a plastic or a metal material having perforations 7 defined therein or formed from a slotted liner or formed from a wire wrapped screen. Particularly, the perforations 7 have a substantially circular cross-section. For example, the perforations 7 may have a diameter from about 0.004 inches to about 0.100 inches, e.g., from about 0.004 inches to about 0.095 inches, from about 0.004 inches to about 0.090 inches, from about 0.004 inches to about 0.085 inches, from about 0.004 inches to about 0.080 inches, from about 0.004 inches to about 0.075 inches, from about 0.004 inches to about 0.070 inches, from about 0.004 inches to about 0.065 inches, from about 0.004 inches to about 0.064 inches, from about 0.004 inches to about 0.063 inches, from about 0.004 inches to about 0.062 inches, from about 0.004 inches to about 0.060 inches, from about 0.004 inches to about 0.055 inches, from about 0.004 inches to about 0.050 inches, from about 0.004 inches to about 0.045 inches, from about 0.004 inches to about 0.040 inches, from about 0.004 inches to about 0.035 inches, from about 0.004 inches to about 0.030 inches, from about 0.004 inches to about 0.025 inches, from about 0.004 inches to about 0.020 inches, from about 0.004 inches to about 0.018 inches, from about 0.004 inches to about 0.016 inches, from about 0.004 inches to about 0.015 inches, from about 0.004 inches to about 0.014 inches, from about 0.004 inches to about 0.012 inches, from about 0.004 inches to about 0.010 inches, from about 0.004 inches to about 0.008 inches, from about 0.004 inches to about 0.006 inches, from about 0.006 inches to about 0.100 inches, from about 0.006 inches to about 0.095 inches, from about 0.006 inches to about 0.090 inches, from about 0.006 inches to about 0.085 inches, from about 0.006 inches to about 0.080 inches, from about 0.006 inches to about 0.075 inches, from about 0.006 inches to about 0.070 inches, from about 0.006 inches to about 0.065 inches, from about 0.006 inches to about 0.064 inches, from about 0.006 inches to about 0.063 inches, from about 0.006 inches to about 0.062 inches, from about 0.006 inches to about 0.060 inches, from about 0.006 inches to about 0.055 inches, from about 0.006 inches to about 0.050 inches, from about 0.006 inches to about 0.045 inches, from about 0.006 inches to about 0.040 inches, from about 0.006 inches to about 0.035 inches, from about 0.006 inches to about 0.030 inches, from about 0.006 inches to about 0.025 inches, from about 0.006 inches to about 0.020 inches, from about 0.006 inches to about 0.018 inches, from about 0.006 inches to about 0.016 inches, from about 0.006 inches to about 0.015 inches, from about 0.006 inches to about 0.014 inches, from about 0.006 inches to about 0.012 inches, from about 0.006 inches to about 0.010 inches, from about 0.006 inches to about 0.008 inches, from about 0.008 inches to about 0.100 inches, from about 0.008 inches to about 0.095 inches, from about 0.008 inches to about 0.090 inches, from about 0.008 inches to about 0.085 inches, from about 0.008 inches to about 0.080 inches, from about 0.008 inches to about 0.075 inches, from about 0.008 inches to about 0.070 inches, from about 0.008 inches to about 0.065 inches, from about 0.008 inches to about 0.064 inches, from about 0.008 inches to about 0.063 inches, from about 0.008 inches to about 0.062 inches, from about 0.008 inches to about 0.060 inches, from about 0.008 inches to about 0.055 inches, from about 0.008 inches to about 0.050 inches, from about 0.008 inches to about 0.045 inches, from about 0.008 inches to about 0.040 inches, from about 0.008 inches to about 0.035 inches, from about 0.008 inches to about 0.030 inches, from about 0.008 inches to about 0.025 inches, from about 0.008 inches to about 0.020 inches, from about 0.008 inches to about 0.018 inches, from about 0.008 inches to about 0.016 inches, from about 0.008 inches to about 0.015 inches, from about 0.008 inches to about 0.014 inches, from about 0.008 inches to about 0.012 inches, from about 0.008 inches to about 0.010 inches, from about 0.010 inches to about 0.100 inches, from about 0.010 inches to about 0.095 inches, from about 0.010 inches to about 0.090 inches, from about 0.010 inches to about 0.085 inches, from about 0.010 inches to about 0.080 inches, from about 0.010 inches to about 0.075 inches, from about 0.010 inches to about 0.070 inches, from about 0.010 inches to about 0.065 inches, from about 0.010 inches to about 0.064 inches, from about 0.010 inches to about 0.063 inches, from about 0.010 inches to about 0.062 inches, from about 0.010 inches to about 0.060 inches, from about 0.010 inches to about 0.055 inches, from about 0.010 inches to about 0.050 inches, from about 0.010 inches to about 0.045 inches, from about 0.010 inches to about 0.040 inches, from about 0.010 inches to about 0.035 inches, from about 0.010 inches to about 0.030 inches, from about 0.010 inches to about 0.025 inches, from about 0.010 inches to about 0.020 inches, from about 0.010 inches to about 0.018 inches, from about 0.010 inches to about 0.016 inches, from about 0.010 inches to about 0.015 inches, from about 0.010 inches to about 0.014 inches, from about 0.010 inches to about 0.012 inches, from about 0.012 inches to about 0.100 inches, from about 0.012 inches to about 0.095 inches, from about 0.012 inches to about 0.090 inches, from about 0.012 inches to about 0.085 inches, from about 0.012 inches to about 0.080 inches, from about 0.012 inches to about 0.075 inches, from about 0.012 inches to about 0.070 inches, from about 0.012 inches to about 0.065 inches, from about 0.012 inches to about 0.064 inches, from about 0.012 inches to about 0.063 inches, from about 0.012 inches to about 0.062 inches, from about 0.012 inches to about 0.060 inches, from about 0.012 inches to about 0.055 inches, from about 0.012 inches to about 0.050 inches, from about 0.012 inches to about 0.045 inches, from about 0.012 inches to about 0.040 inches, from about 0.012 inches to about 0.035 inches, from about 0.012 inches to about 0.030 inches, from about 0.012 inches to about 0.025 inches, from about 0.012 inches to about 0.020 inches, from about 0.012 inches to about 0.018 inches, from about 0.012 inches to about 0.016 inches, from about 0.012 inches to about 0.015 inches, from about 0.012 inches to about 0.014 inches, from about 0.014 inches to about 0.100 inches, from about 0.014 inches to about 0.095 inches, from about 0.014 inches to about 0.090 inches, from about 0.014 inches to about 0.085 inches, from about 0.014 inches to about 0.080 inches, from about 0.014 inches to about 0.075 inches, from about 0.014 inches to about 0.070 inches, from about 0.014 inches to about 0.065 inches, from about 0.014 inches to about 0.064 inches, from about 0.014 inches to about 0.063 inches, from about 0.014 inches to about 0.062 inches, from about 0.014 inches to about 0.060 inches, from about 0.014 inches to about 0.055 inches, from about 0.014 inches to about 0.050 inches, from about 0.014 inches to about 0.045 inches, from about 0.014 inches to about 0.040 inches, from about 0.014 inches to about 0.035 inches, from about 0.014 inches to about 0.030 inches, from about 0.014 inches to about 0.025 inches, from about 0.014 inches to about 0.020 inches, from about 0.014 inches to about 0.018 inches, from about 0.014 inches to about 0.016 inches, from about 0.014 inches to about 0.015 inches, from about 0.015 inches to about 0.100 inches, from about 0.015 inches to about 0.095 inches, from about 0.015 inches to about 0.090 inches, from about 0.015 inches to about 0.085 inches, from about 0.015 inches to about 0.080 inches, from about 0.015 inches to about 0.075 inches, from about 0.015 inches to about 0.070 inches, from about 0.015 inches to about 0.065 inches, from about 0.015 inches to about 0.064 inches, from about 0.015 inches to about 0.063 inches, from about 0.015 inches to about 0.062 inches, from about 0.015 inches to about 0.060 inches, from about 0.015 inches to about 0.055 inches, from about 0.015 inches to about 0.050 inches, from about 0.015 inches to about 0.045 inches, from about 0.015 inches to about 0.040 inches, from about 0.015 inches to about 0.035 inches, from about 0.015 inches to about 0.030 inches, from about 0.015 inches to about 0.025 inches, from about 0.015 inches to about 0.020 inches, from about 0.015 inches to about 0.018 inches, from about 0.015 inches to about 0.016 inches, from about 0.016 inches to about 0.100 inches, from about 0.016 inches to about 0.095 inches, from about 0.016 inches to about 0.090 inches, from about 0.016 inches to about 0.085 inches, from about 0.016 inches to about 0.080 inches, from about 0.016 inches to about 0.075 inches, from about 0.016 inches to about 0.070 inches, from about 0.016 inches to about 0.065 inches, from about 0.016 inches to about 0.064 inches, from about 0.016 inches to about 0.063 inches, from about 0.016 inches to about 0.062 inches, from about 0.016 inches to about 0.060 inches, from about 0.016 inches to about 0.055 inches, from about 0.016 inches to about 0.050 inches, from about 0.016 inches to about 0.045 inches, from about 0.016 inches to about 0.040 inches, from about 0.016 inches to about 0.035 inches, from about 0.016 inches to about 0.030 inches, from about 0.016 inches to about 0.025 inches, from about 0.016 inches to about 0.020 inches, from about 0.016 inches to about 0.018 inches, from about 0.018 inches to about 0.100 inches, from about 0.018 inches to about 0.095 inches, from about 0.018 inches to about 0.090 inches, from about 0.018 inches to about 0.085 inches, from about 0.018 inches to about 0.080 inches, from about 0.018 inches to about 0.075 inches, from about 0.018 inches to about 0.070 inches, from about 0.018 inches to about 0.065 inches, from about 0.018 inches to about 0.064 inches, from about 0.018 inches to about 0.063 inches, from about 0.018 inches to about 0.062 inches, from about 0.018 inches to about 0.060 inches, from about 0.018 inches to about 0.055 inches, from about 0.018 inches to about 0.050 inches, from about 0.018 inches to about 0.045 inches, from about 0.018 inches to about 0.040 inches, from about 0.018 inches to about 0.035 inches, from about 0.018 inches to about 0.030 inches, from about 0.018 inches to about 0.025 inches, from about 0.018 inches to about 0.020 inches, from about 0.020 inches to about 0.100 inches, from about 0.020 inches to about 0.095 inches, from about 0.020 inches to about 0.090 inches, from about 0.020 inches to about 0.085 inches, from about 0.020 inches to about 0.080 inches, from about 0.020 inches to about 0.075 inches, from about 0.020 inches to about 0.070 inches, from about 0.020 inches to about 0.065 inches, from about 0.020 inches to about 0.064 inches, from about 0.020 inches to about 0.063 inches, from about 0.020 inches to about 0.062 inches, from about 0.020 inches to about 0.060 inches, from about 0.020 inches to about 0.055 inches, from about 0.020 inches to about 0.050 inches, from about 0.020 inches to about 0.045 inches, from about 0.020 inches to about 0.040 inches, from about 0.020 inches to about 0.035 inches, from about 0.020 inches to about 0.030 inches, from about 0.020 inches to about 0.025 inches, from about 0.025 inches to about 0.100 inches, from about 0.025 inches to about 0.095 inches, from about 0.025 inches to about 0.090 inches, from about 0.025 inches to about 0.085 inches, from about 0.025 inches to about 0.080 inches, from about 0.025 inches to about 0.075 inches, from about 0.025 inches to about 0.070 inches, from about 0.025 inches to about 0.065 inches, from about 0.025 inches to about 0.064 inches, from about 0.025 inches to about 0.063 inches, from about 0.025 inches to about 0.062 inches, from about 0.025 inches to about 0.060 inches, from about 0.025 inches to about 0.055 inches, from about 0.025 inches to about 0.050 inches, from about 0.025 inches to about 0.045 inches, from about 0.025 inches to about 0.040 inches, from about 0.025 inches to about 0.035 inches, from about 0.025 inches to about 0.030 inches, from about 0.030 inches to about 0.100 inches, from about 0.030 inches to about 0.095 inches, from about 0.030 inches to about 0.090 inches, from about 0.030 inches to about 0.085 inches, from about 0.030 inches to about 0.080 inches, from about 0.030 inches to about 0.075 inches, from about 0.030 inches to about 0.070 inches, from about 0.030 inches to about 0.065 inches, from about 0.030 inches to about 0.064 inches, from about 0.030 inches to about 0.063 inches, from about 0.030 inches to about 0.062 inches, from about 0.030 inches to about 0.060 inches, from about 0.030 inches to about 0.055 inches, from about 0.030 inches to about 0.050 inches, from about 0.030 inches to about 0.045 inches, from about 0.030 inches to about 0.040 inches, from about 0.030 inches to about 0.035 inches, from about 0.035 inches to about 0.100 inches, from about 0.035 inches to about 0.095 inches, from about 0.035 inches to about 0.090 inches, from about 0.035 inches to about 0.085 inches, from about 0.035 inches to about 0.080 inches, from about 0.035 inches to about 0.075 inches, from about 0.035 inches to about 0.070 inches, from about 0.035 inches to about 0.065 inches, from about 0.035 inches to about 0.064 inches, from about 0.035 inches to about 0.063 inches, from about 0.035 inches to about 0.062 inches, from about 0.035 inches to about 0.060 inches, from about 0.035 inches to about 0.055 inches, from about 0.035 inches to about 0.050 inches, from about 0.035 inches to about 0.045 inches, from about 0.035 inches to about 0.040 inches, from about 0.040 inches to about 0.100 inches, from about 0.040 inches to about 0.095 inches, from about 0.040 inches to about 0.090 inches, from about 0.040 inches to about 0.085 inches, from about 0.040 inches to about 0.080 inches, from about 0.040 inches to about 0.075 inches, from about 0.040 inches to about 0.070 inches, from about 0.040 inches to about 0.065 inches, from about 0.040 inches to about 0.064 inches, from about 0.040 inches to about 0.063 inches, from about 0.040 inches to about 0.062 inches, from about 0.040 inches to about 0.060 inches, from about 0.040 inches to about 0.055 inches, from about 0.040 inches to about 0.050 inches, from about 0.040 inches to about 0.045 inches, from about 0.045 inches to about 0.100 inches, from about 0.045 inches to about 0.095 inches, from about 0.045 inches to about 0.090 inches, from about 0.045 inches to about 0.085 inches, from about 0.045 inches to about 0.080 inches, from about 0.045 inches to about 0.075 inches, from about 0.045 inches to about 0.070 inches, from about 0.045 inches to about 0.065 inches, from about 0.045 inches to about 0.064 inches, from about 0.045 inches to about 0.063 inches, from about 0.045 inches to about 0.062 inches, from about 0.045 inches to about 0.060 inches, from about 0.045 inches to about 0.055 inches, from about 0.045 inches to about 0.050 inches, from about 0.050 inches to about 0.100 inches, from about 0.050 inches to about 0.095 inches, from about 0.050 inches to about 0.090 inches, from about 0.050 inches to about 0.085 inches, from about 0.050 inches to about 0.080 inches, from about 0.050 inches to about 0.075 inches, from about 0.050 inches to about 0.070 inches, from about 0.050 inches to about 0.065 inches, from about 0.050 inches to about 0.064 inches, from about 0.050 inches to about 0.063 inches, from about 0.050 inches to about 0.062 inches, from about 0.050 inches to about 0.060 inches, from about 0.050 inches to about 0.055 inches, from about 0.055 inches to about 0.100 inches, from about 0.055 inches to about 0.095 inches, from about 0.055 inches to about 0.090 inches, from about 0.055 inches to about 0.085 inches, from about 0.055 inches to about 0.080 inches, from about 0.055 inches to about 0.075 inches, from about 0.055 inches to about 0.070 inches, from about 0.055 inches to about 0.065 inches, from about 0.055 inches to about 0.064 inches, from about 0.055 inches to about 0.063 inches, from about 0.055 inches to about 0.062 inches, from about 0.055 inches to about 0.060 inches, from about 0.060 inches to about 0.100 inches, from about 0.060 inches to about 0.095 inches, from about 0.060 inches to about 0.090 inches, from about 0.060 inches to about 0.085 inches, from about 0.060 inches to about 0.080 inches, from about 0.060 inches to about 0.075 inches, from about 0.060 inches to about 0.070 inches, from about 0.060 inches to about 0.065 inches, from about 0.060 inches to about 0.064 inches, from about 0.060 inches to about 0.063 inches, from about 0.060 inches to about 0.062 inches, from about 0.062 inches to about 0.100 inches, from about 0.062 inches to about 0.095 inches, from about 0.062 inches to about 0.090 inches, from about 0.062 inches to about 0.085 inches, from about 0.062 inches to about 0.080 inches, from about 0.062 inches to about 0.075 inches, from about 0.062 inches to about 0.070 inches, from about 0.062 inches to about 0.065 inches, from about 0.062 inches to about 0.064 inches, from about 0.062 inches to about 0.063 inches, from about 0.063 inches to about 0.100 inches, from about 0.063 inches to about 0.095 inches, from about 0.063 inches to about 0.090 inches, from about 0.063 inches to about 0.085 inches, from about 0.063 inches to about 0.080 inches, from about 0.063 inches to about 0.075 inches, from about 0.063 inches to about 0.070 inches, from about 0.063 inches to about 0.065 inches, from about 0.063 inches to about 0.064 inches, from about 0.064 inches to about 0.100 inches, from about 0.064 inches to about 0.095 inches, from about 0.064 inches to about 0.090 inches, from about 0.064 inches to about 0.085 inches, from about 0.064 inches to about 0.080 inches, from about 0.064 inches to about 0.075 inches, from about 0.064 inches to about 0.070 inches, from about 0.064 inches to about 0.065 inches, from about 0.065 inches to about 0.100 inches, from about 0.065 inches to about 0.095 inches, from about 0.065 inches to about 0.090 inches, from about 0.065 inches to about 0.085 inches, from about 0.065 inches to about 0.080 inches, from about 0.065 inches to about 0.075 inches, from about 0.065 inches to about 0.070 inches, from about 0.070 inches to about 0.100 inches, from about 0.070 inches to about 0.095 inches, from about 0.070 inches to about 0.090 inches, from about 0.070 inches to about 0.085 inches, from about 0.070 inches to about 0.080 inches, from about 0.070 inches to about 0.075 inches, from about 0.075 inches to about 0.100 inches, from about 0.075 inches to about 0.095 inches, from about 0.075 inches to about 0.090 inches, from about 0.075 inches to about 0.085 inches, from about 0.075 inches to about 0.080 inches, from about 0.080 inches to about 0.100 inches, from about 0.080 inches to about 0.095 inches, from about 0.080 inches to about 0.090 inches, from about 0.080 inches to about 0.085 inches, from about 0.085 inches to about 0.100 inches, from about 0.085 inches to about 0.095 inches, from about 0.085 inches to about 0.090 inches, from about 0.090 inches to about 0.100 inches, from about 0.090 inches to about 0.095 inches, or from about 0.095 inches to about 0.100 inches. In particular, the perforations 7 can have a diameter from about 0.015 inches to about 0.063 inches.

The number of perforations 7 present in the at least one stripping chamber 4 depends upon an open area of the least one stripping chamber 4 required for effective stripping of the process fluid from the solid particles (e.g., catalyst). As used herein, the term "open area" refers to the combined area of the openings of the perforations 7. An open area of the perforations 7 may define from about 5.0% to about 95%, e.g., from about 5.0% to about 90%, from about 5.0% to about 85%, from about 5.0% to about 80%, from about 5.0% to about 75%, from about 5.0% to about 70%, from about 5.0% to about 65%, from about 5.0% to about 60%, from about 5.0% to about 54%, from about 5.0% to about 50%, from about 5.0% to about 45%, from about 5.0% to about 40%, from about 5.0% to about 39%, from about 5.0% to about 38%, from about 5.0% to about 37%, from about 5.0% to about 36%, from about 5.0% to about 35%, from about 5.0% to about 34%, from about 5.0% to about 33%, from about 5.0% to about 32%, from about 5.0% to about 31%, from about 5.0% to about 30%, from about 5.0% to about 25%, from about 5.0% to about 20%, from about 5.0% to about 15%, from about 5.0% to about 10%, from about 10% to about 95%, from about 10% to about 90%, from about 10% to about 85%, from about 10% to about 80%, from about 10% to about 75%, from about 10% to about 70%, from about 10% to about 65%, from about 10% to about 60%, from about 10% to about 54%, from about 10% to about 50%, from about 10% to about 45%, from about 10% to about 40%, from about 10% to about 39%, from about 10% to about 38%, from about 10% to about 37%, from about 10% to about 36%, from about 10% to about 35%, from about 10% to about 34%, from about 10% to about 33%, from about 10% to about 32%, from about 10% to about 31%, from about 10% to about 30%, from about 10% to about 25%, from about 10% to about 20%, from about 10% to about 15%, from about 15% to about 95%, from about 15% to about 90%, from about 15% to about 85%, from about 15% to about 80%, from about 15% to about 75%, from about 15% to about 70%, from about 15% to about 65%, from about 15% to about 60%, from about 15% to about 54%, from about 15% to about 50%, from about 15% to about 45%, from about 15% to about 40%, from about 15% to about 39%, from about 15% to about 38%, from about 15% to about 37%, from about 15% to about 36%, from about 15% to about 35%, from about 15% to about 34%, from about 15% to about 33%, from about 15% to about 32%, from about 15% to about 31%, from about 15% to about 30%, from about 15% to about 25%, from about 15% to about 20%, from about 20% to about 95%, from about 20% to about 90%, from about 20% to about 85%, from about 20% to about 80%, from about 20% to about 75%, from about 20% to about 70%, from about 20% to about 65%, from about 20% to about 60%, from about 20% to about 54%, from about 20% to about 50%, from about 20% to about 45%, from about 20% to about 40%, from about 20% to about 39%, from about 20% to about 38%, from about 20% to about 37%, from about 20% to about 36%, from about 20% to about 35%, from about 20% to about 34%, from about 20% to about 33%, from about 20% to about 32%, from about 20% to about 31%, from about 20% to about 30%, from about 20% to about 25%, from about 25% to about 95%, from about 25% to about 90%, from about 25% to about 85%, from about 25% to about 80%, from about 25% to about 75%, from about 25% to about 70%, from about 25% to about 65%, from about 25% to about 60%, from about 25% to about 54%, from about 25% to about 50%, from about 25% to about 45%, from about 25% to about 40%, from about 25% to about 39%, from about 25% to about 38%, from about 25% to about 37%, from about 25% to about 36%, from about 25% to about 35%, from about 25% to about 34%, from about 25% to about 33%, from about 25% to about 32%, from about 25% to about 31%, from about 25% to about 30%, from about 30% to about 95%, from about 30% to about 90%, from about 30% to about 85%, from about 30% to about 80%, from about 30% to about 75%, from about 30% to about 70%, from about 30% to about 65%, from about 30% to about 60%, from about 30% to about 54%, from about 30% to about 50%, from about 30% to about 45%, from about 30% to about 40%, from about 30% to about 39%, from about 30% to about 38%, from about 30% to about 37%, from about 30% to about 36%, from about 30% to about 35%, from about 30% to about 34%, from about 30% to about 33%, from about 30% to about 32%, from about 30% to about 31%, from about 31% to about 95%, from about 31% to about 90%, from about 31% to about 85%, from about 31% to about 80%, from about 31% to about 75%, from about 31% to about 70%, from about 31% to about 65%, from about 31% to about 60%, from about 31% to about 54%, from about 31% to about 50%, from about 31% to about 45%, from about 31% to about 40%, from about 31% to about 39%, from about 31% to about 38%, from about 31% to about 37%, from about 31% to about 36%, from about 20% to about 35%, from about 31% to about 34%, from about 31% to about 33%, from about 31% to about 32%, from about 32% to about 95%, from about 32% to about 90%, from about 32% to about 85%, from about 32% to about 80%, from about 32% to about 75%, from about 32% to about 70%, from about 32% to about 65%, from about 32% to about 60%, from about 32% to about 54%, from about 32% to about 50%, from about 32% to about 45%, from about 32% to about 40%, from about 32% to about 39%, from about 32% to about 38%, from about 32% to about 37%, from about 32% to about 36%, from about 32% to about 35%, from about 32% to about 34%, from about 32% to about 33%, from about 33% to about 95%, from about 33% to about 90%, from about 33% to about 85%, from about 33% to about 80%, from about 33% to about 75%, from about 33% to about 70%, from about 33% to about 65%, from about 33% to about 60%, from about 33% to about 54%, from about 33% to about 50%, from about 33% to about 45%, from about 33% to about 40%, from about 33% to about 39%, from about 33% to about 38%, from about 33% to about 37%, from about 33% to about 36%, from about 33% to about 35%, from about 33% to about 34%, from about 34% to about 95%, from about 34% to about 90%, from about 34% to about 85%, from about 34% to about 80%, from about 34% to about 75%, from about 34% to about 70%, from about 34% to about 65%, from about 34% to about 60%, from about 34% to about 54%, from about 34% to about 50%, from about 34% to about 45%, from about 34% to about 40%, from about 34% to about 39%, from about 34% to about 38%, from about 20% to about 37%, from about 20% to about 36%, from about 34% to about 35%, from about 35% to about 95%, from about 35% to about 90%, from about 35% to about 85%, from about 35% to about 80%, from about 2035 to about 75%, from about 35% to about 70%, from about 35% to about 65%, from about 35% to about 60%, from about 35% to about 54%, from about 35% to about 50%, from about 35% to about 45%, from about 35% to about 40%, from about 35% to about 39%, from about 35% to about 38%, from about 35% to about 37%, from about 35% to about 36%, from about 36% to about 95%, from about 36% to about 90%, from about 36% to about 85%, from about 36% to about 80%, from about 36% to about 75%, from about 6% to about 70%, from about 36% to about 65%, from about 36% to about 60%, from about 36% to about 54%, from about 36% to about 50%, from about 36% to about 45%, from about 36% to about 40%, from about 36% to about 39%, from about 36% to about 38%, from about 36% to about 37%, from about 37% to about 95%, from about 37% to about 90%, from about 37% to about 85%, from about 37% to about 80%, from about 37% to about 75%, from about 37% to about 70%, from about 37% to about 65%, from about 37% to about 60%, from about 37% to about 54%, from about 37% to about 50%, from about 37% to about 45%, from about 37% to about 40%, from about 37% to about 39%, from about 37% to about 38%, from about 38% to about 95%, from about 38% to about 90%, from about 38% to about 85%, from about 38% to about 80%, from about 38% to about 75%, from about 38% to about 70%, from about 38% to about 65%, from about 38% to about 60%, from about 38% to about 54%, from about 38% to about 50%, from about 38% to about 45%, from about 38% to about 40%, from about 38% to about 39%, from about 39% to about 95%, from about 39% to about 90%, from about 39% to about 85%, from about 39% to about 80%, from about 39% to about 75%, from about 39% to about 70%, from about 39% to about 65%, from about 39% to about 60%, from about 39% to about 54%, from about 39% to about 50%, from about 39% to about 45%, from about 39% to about 40%, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 54%, from about 40% to about 50%, from about 40% to about 45%, from about 45% to about 95%, from about 45% to about 90%, from about 45% to about 85%, from about 45% to about 80%, from about 45% to about 75%, from about 45% to about 70%, from about 45% to about 65%, from about 45% to about 60%, from about 45% to about 54%, from about 45% to about 50%, from about 50% to about 95%, from about 50% to about 90%, from about 50% to about 85%, from about 50% to about 80%, from about 50% to about 75%, from about 50% to about 70%, from about 50% to about 65%, from about 50% to about 60%, from about 50% to about 54%, from about 54% to about 95%, from about 54% to about 90%, from about 54% to about 85%, from about 54% to about 80%, from about 54% to about 75%, from about 54% to about 70%, from about 54% to about 65%, from about 54% to about 60%, from about 60% to about 95%, from about 60% to about 90%, from about 60% to about 85%, from about 60% to about 80%, from about 60% to about 75%, from about 60% to about 70%, from about 60% to about 65%, from about 65% to about 95%, from about 65% to about 90%, from about 65% to about 85%, from about 65% to about 80%, from about 65% to about 75%, from about 65% to about 70%, from about 65% to about 95%, from about 65% to about 90%, from about 65% to about 85%, from about 65% to about 80%, from about 65% to about 75%, from about 65% to about 70%, from about 70% to about 95%, from about 70% to about 90%, from about 70% to about 85%, from about 70% to about 80%, from about 70% to about 75%, from about 75% to about 95%, from about 75% to about 90%, from about 75% to about 85%, from about 75% to about 80%, from about 80% to about 95%, from about 80% to about 90%, from about 80% to about 85%, from about 85% to about 95%, from about 85% to about 90%, or from about 90% to about 95% of the total surface of area of the at least one stripping chamber 4.

Figure 2:
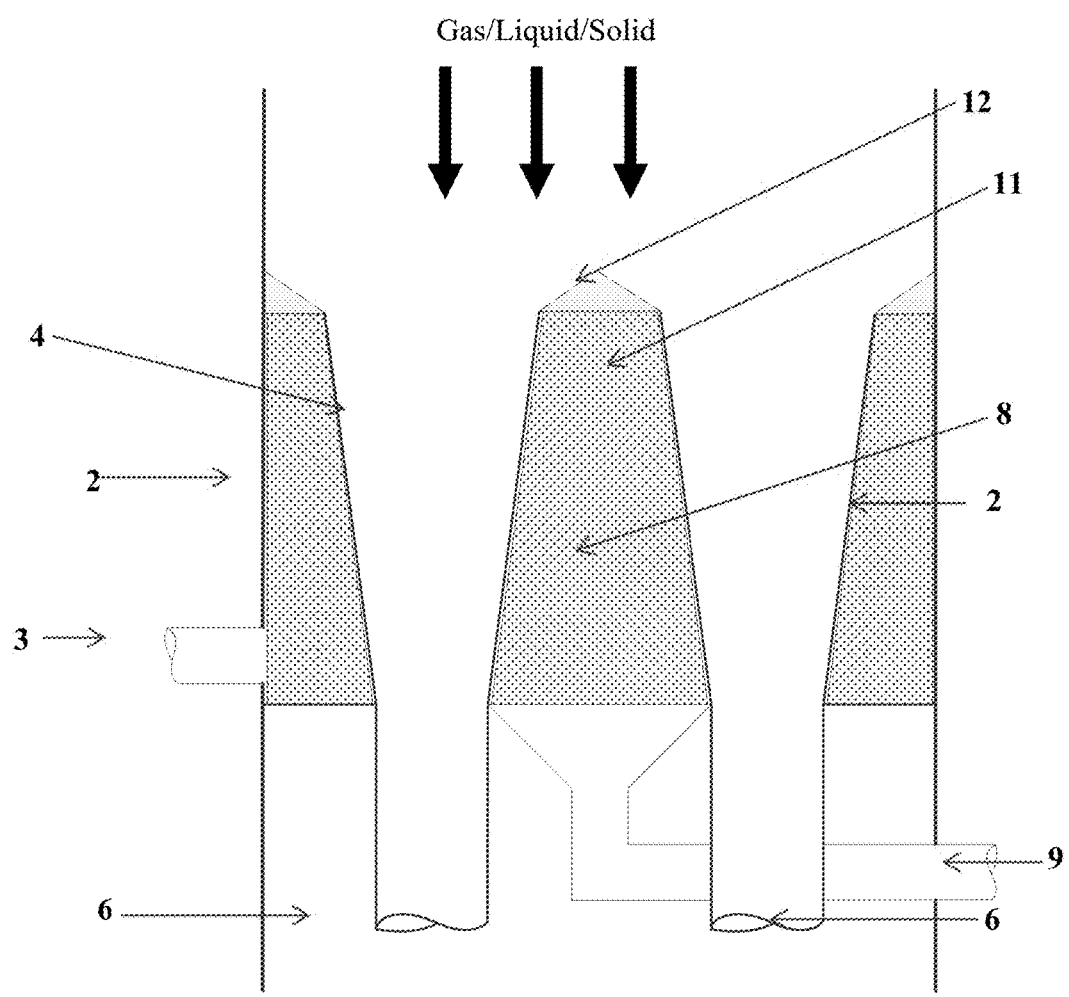
FIG. 2 illustrates a cross-section view of an embodiment of a multiphase separator 1 with more than one stripping chamber 4.

Additionally or alternatively, the at least one stripping chamber 4 can comprise a stripping interface section 11 and/or a guide section 12, as shown in FIG. 2. The stripping interface section 11 may have a first angle and the guide section 12 may have a second angle. The first angle may be less than or equal to, or greater than or equal to the second angle. In particular the first angle can be less than or equal to the second angle.

The first angle and/or the second angle may each independently be from about 1.0° to about 70°, e.g., from about 1.0° to about 65°, from about 1.0° to about 60°, from about 1.0° to about 55°, from about 1.0° to about 50°, from about 1.0° to about 45°, from about 1.0° to about 40°, from about 1.0° to about 35°, from about 1.0° to about 30°, from about 1.0° to about 25°, from about 1.0° to about 20°, from about 1.0° to about 15°, from about 1.0° to about 10°, from about 1.0° to about 9.0°, from about 1.0° to about 8.0°, from about 1.0° to about 7.5°, from about 1.0° to about 7.0°, from about 1.0° to about 5.0°, from about 1.0° to about 4.0°, from about 1.0° to about 3.0°, from about 1.0° to about 2.0°, from about 2.0° to about 70°, from about 2.0° to about 65°, from about 2.0° to about 60°, from about 2.0° to about 55°, from about 2.0° to about 50°, from about 2.0° to about 45°, from about 2.0° to about 40°, from about 2.0° to about 35°, from about 2.0° to about 30°, from about 2.0° to about 25°, from about 2.0° to about 20°, from about 2.0° to about 15°, from about 2.0° to about 10°, from about 2.0° to about 9.0°, from about 2.0° to about 8.0°, from about 2.0° to about 7.5°, from about 2.0° to about 7.0°, from about 2.0° to about 5.0°, from about 2.0° to about 4.0°, from about 2.0° to about 3.0°, from about 3.0° to about 70°, from about 3.0° to about 65°, from about 3.0° to about 60°, from about 3.0° to about 55°, from about 3.0° to about 50°, from about 3.0° to about 45°, from about 3.0° to about 40°, from about 3.0° to about 35°, from about 3.0° to about 30°, from about 3.0° to about 25°, from about 3.0° to about 20°, from about 3.0° to about 15°, from about 3.0° to about 10°, from about 3.0° to about 9.0°, from about 3.0° to about 8.0°, from about 3.0° to about 7.5°, from about 3.0° to about 7.0°, from about 3.0° to about 5.0°, from about 3.0° to about 4.0°, from about 4.0° to about 70°, from about 4.0° to about 65°, from about 4.0° to about 60°, from about 4.0° to about 55°, from about 4.0° to about 50°, from about 4.0° to about 45°, from about 4.0° to about 40°, from about 4.0° to about 35°, from about 4.0° to about 30°, from about 4.0° to about 25°, from about 4.0° to about 20°, from about 4.0° to about 15°, from about 4.0° to about 10°, from about 4.0° to about 9.0°, from about 4.0° to about 8.0°, from about 4.0° to about 7.5°, from about 4.0° to about 7.0°, from about 4.0° to about 5.0°, from about 5.0° to about 70°, from about 5.0° to about 65°, from about 5.0° to about 60°, from about 5.0° to about 55°, from about 5.0° to about 50°, from about 5.0° to about 45°, from about 5.0° to about 40°, from about 5.0° to about 35°, from about 5.0° to about 30°, from about 5.0° to about 25°, from about 5.0° to about 20°, from about 5.0° to about 15°, from about 5.0° to about 10°, from about 5.0° to about 9.0°, from about 5.0° to about 8.0°, from about 5.0° to about 7.5°, from about 5.0° to about 7.0°, from about 7.0° to about 70°, from about 7.0° to about 65°, from about 7.0° to about 60°, from about 7.0° to about 55°, from about 7.0° to about 50°, from about 7.0° to about 45°, from about 7.0° to about 40°, from about 7.0° to about 35°, from about 7.0° to about 30°, from about 7.0° to about 25°, from about 7.0° to about 20°, from about 7.0° to about 15°, from about 7.0° to about 10°, from about 7.0° to about 9.0°, from about 7.0° to about 8.0°, from about 7.0° to about 7.5°, from about 7.5° to about 70°, from about 7.5° to about 65°, from about 7.5° to about 60°, from about 7.5° to about 55°, from about 7.5° to about 50°, from about 7.5° to about 45°, from about 7.5° to about 40°, from about 7.5° to about 35°, from about 7.5° to about 30°, from about 7.5° to about 25°, from about 7.5° to about 20°, from about 7.5° to about 15°, from about 7.5° to about 10°, from about 7.5° to about 9.0°, from about 7.5° to about 8.0°, from about 8.0° to about 70°, from about 8.0° to about 65°, from about 8.0° to about 60°, from about 8.0° to about 55°, from about 8.0° to about 50°, from about 8.0° to about 45°, from about 8.0° to about 40°, from about 8.0° to about 35°, from about 8.0° to about 30°, from about 8.0° to about 25°, from about 8.0° to about 20°, from about 8.0° to about 15°, from about 8.0° to about 10°, from about 8.0° to about 9.0°, from about 9.0° to about 70°, from about 9.0° to about 65°, from about 9.0° to about 60°, from about 9.0° to about 55°, from about 9.0° to about 50°, from about 9.0° to about 45°, from about 9.0° to about 40°, from about 9.0° to about 35°, from about 9.0° to about 30°, from about 9.0° to about 25°, from about 9.0° to about 20°, from about 9.0° to about 15°, from about 9.0° to about 10°, from about 10° to about 70°, from about 10° to about 65°, from about 10° to about 60°, from about 10° to about 55°, from about 10° to about 50°, from about 10° to about 45°, from about 10° to about 40°, from about 10° to about 35°, from about 10° to about 30°, from about 10° to about 25°, from about 10° to about 20°, from about 10° to about 15°, from about 15° to about 70°, from about 15° to about 65°, from about 15° to about 60°, from about 5° to about 55°, from about 15° to about 50°, from about 15° to about 45°, from about 15° to about 40°, from about 15° to about 35°, from about 15° to about 30°, from about 15° to about 25°, from about 15° to about 20°, from about 20° to about 70°, from about 20° to about 65°, from about 20° to about 60°, from about 20° to about 55°, from about 20° to about 50°, from about 20° to about 45°, from about 20° to about 40°, from about 20° to about 35°, from about 20° to about 30°, from about 20° to about 25°, from about 25° to about 70°, from about 25° to about 65°, from about 25° to about 60°, from about 25° to about 55°, from about 25° to about 50°, from about 25° to about 45°, from about 25° to about 40°, from about 25° to about 35°, from about 25° to about 30°, from about 30° to about 70°, from about 30° to about 65°, from about 30° to about 60°, from about 30° to about 55°, from about 30° to about 50°, from about 30° to about 45°, from about 30° to about 40°, from about 30° to about 35°, from about 35° to about 70°, from about 35° to about 65°, from about 35° to about 60°, from about 35° to about 55°, from about 35° to about 50°, from about 35° to about 45°, from about 35° to about 40°, from about 40° to about 70°, from about 40° to about 65°, from about 40° to about 60°, from about 40° to about 55°, from about 40° to about 50°, from about 40° to about 45°, from about 45° to about 70°, from about 45° to about 65°, from about 45° to about 60°, from about 45° to about 55°, from about 45° to about 50°, from about 50° to about 70°, from about 50° to about 65°, from about 50° to about 60°, from about 50° to about 55°, from about 55° to about 70°, from about 55° to about 65°, from about 55° to about 60°, from about 60° to about 70°, from about 60° to about 65°, or from about 65° to about 70°. In particular, the first angle can be from about 5.0° to about 30° and/or the second angle may be from about 7.0° to about 45°.

Additionally or alternatively, the at least one stripping chamber 4 can includes multiple stripping chambers 4, e.g. at least two stripping chambers 4, at least three stripping chambers 4, at least four stripping chambers 4, at least five stripping chambers 4, at least six stripping chambers 4, at least seven stripping chambers 4, at least eight stripping chambers 4, at least nine stripping chambers 4, at least ten stripping chambers 4, at least twelve stripping chambers 4, at least fourteen stripping chambers 4, at least sixteen stripping chambers 4, at least eighteen stripping chambers 4, at least twenty stripping chambers 4, etc. When multiple stripping chambers 4 are present, each stripping chamber 4 may have its own inlet chamber 2 or the multiple stripping chambers 4 may share one or more inlet chambers 2.

E. Collection Chamber

Additionally or alternatively, the multiphase separator 1 may further comprise at least one collection chamber 8 comprising at least one outlet 9.

Additionally or alternatively, a portion of the at least one collection chamber 8 may be sloped in order to allow for gravitational discharge of the stripped process fluid and/or stripping fluid through the at least one outlet 9.

In various aspects, the at least one stripping chamber 4 may generally be disposed between the at least one inlet chamber 2 and the at least one collection chamber 8 and at least a portion of the perforations 7 may be in fluid communication with the at least one inlet chamber 2 and the at least one collection chamber 8 such that the stripping fluid may enter the at least one inlet chamber 2 and may flow through the perforations 7 into the at least one stripping chamber 4 and into the at least one collection chamber 8. Additionally, the stripped process fluid may flow from the at least one stripping chamber 4 through the perforations 7 into the at least one collection chamber 8.

Figure 3:
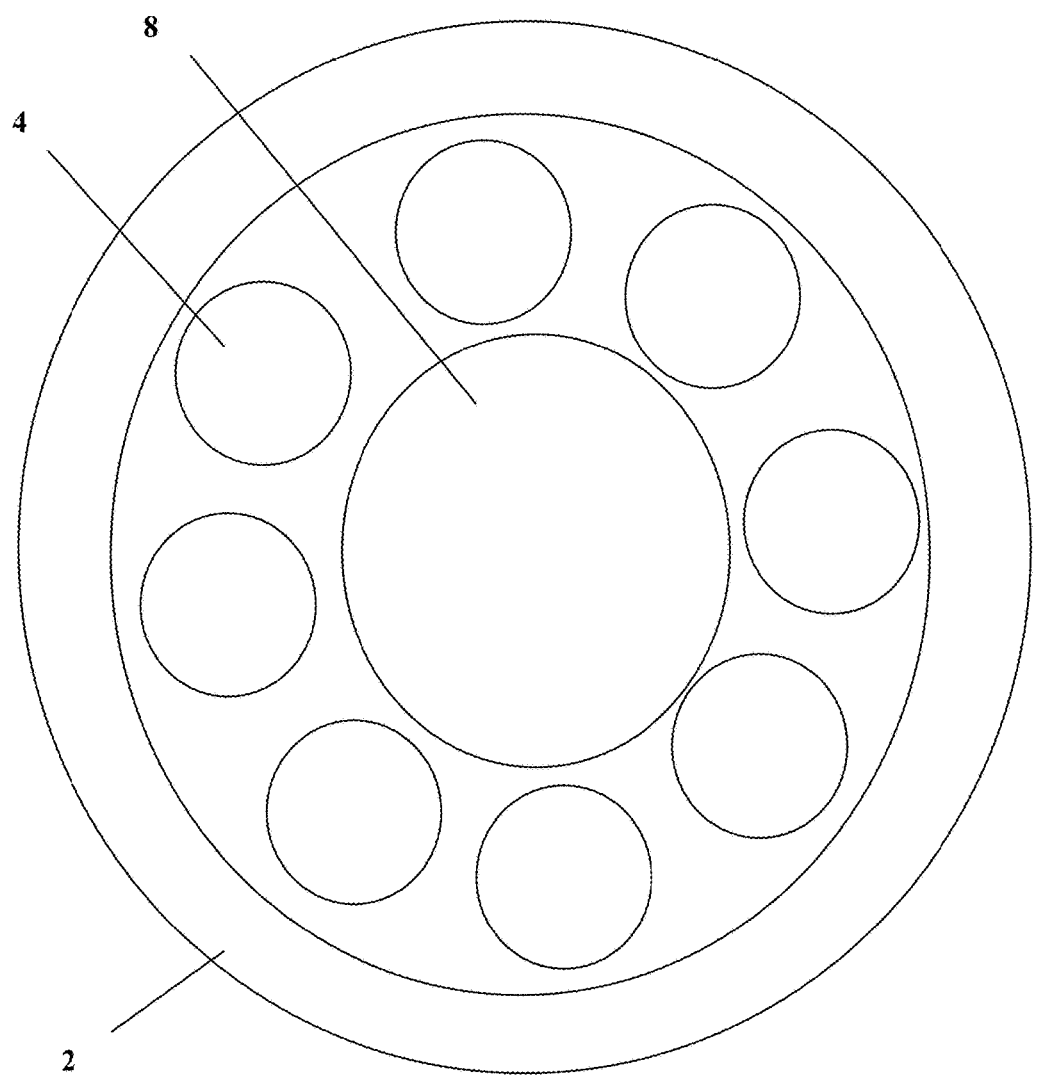
FIG. 3 provides a top view of an embodiment of multiple stripping chambers 4 generally disposed concentrically around at least one collection chamber 8.

Additionally or alternatively, if multiple stripping chambers 4 are present, the multiple stripping chambers 4 may be generally disposed concentrically around the at least one collection chamber 8, as shown in FIG. 3.

F. Stripping Fluid

The stripping fluid introduced into the at least one inlet chamber 2 via the at least one inlet 3 is capable of stripping (i.e., removing) the process fluid from the solid particles (e.g., catalyst). The stripping fluid may be in a liquid state and/or a gas state, particularly in a gas state. Suitable stripping fluids can include, but are not limited to an inert gas (e.g., nitrogen, argon, etc.), methane, carbon dioxide, methanol, steam, and/or a mixture thereof.

The stripping fluid may generally flow in a direction co-current or cross-current to a direction of a flow of the solid particles (e.g. catalyst). As used herein, the term "co-current" refers to a flow parallel in direction to the flow of the solid particles (e.g., catalyst). As used herein, the term "cross-current" refers to a flow orthogonal in direction to the flow of the solid particles. In particular, the stripping fluid generally flows in a direction cross-current to a direction of a flow of the solid particles (e.g., catalyst).

Additionally or alternatively, the stripping fluid may enter the at least one inlet chamber 2 at a flow rate capable of causing the following: (i) flow of the stripping fluid through the perforations 7 of the at least one stripping chamber 4; (ii) stripping of at least a portion of the process fluid from the solid particles (e.g., catalyst) in the at least one stripping chamber 4; and/or (iii) flow of the stripped process fluid and the stripping fluid into the at least one collection chamber 8. For example, the stripping fluid may enter the at least one inlet chamber 2 at a flow rate from about 1.0% to about 2500%, e.g., from about 1.0% to about 2000%, from about 1.0% to about 1750%, from about 1.0% to about 1500%, from about 1.0% to about 1250%, from about 1.0% to about 1000%, from about 1.0% to about 800%, from about 1.0% to about 600%, from about 1.0% to about 500%, from about 1.0% to about 400%, from about 1.0% to about 300%, from about 1.0% to about 250%, from about 1.0% to about 200%, from about 1.0% to about 150%, from about 1.0% to about 100%, from about 1.0% to about 75%, from about 1.0% to about 50%, from about 1.0% to about 25%, from about 1.0% to about 10%, from about 1.0% to about 5.0%, from about 5.0% to about 2500%, from about 5.0% to about 2000%, from about 5.0% to about 1750%, from about 5.0% to about 1500%, from about 5.0% to about 1250%, from about 5.0% to about 1000%, from about 5.0% to about 800%, from about 5.0% to about 600%, from about 5.0% to about 500%, from about 5.0% to about 400%, from about 5.0% to about 300%, from about 5.0% to about 250%, from about 5.0% to about 200%, from about 5.0% to about 150%, from about 5.0% to about 100%, from about 5.0% to about 75%, from about 5.0% to about 50%, from about 5.0% to about 25%, from about 5.0% to about 10%, from about 10% to about 2500%, from about 10% to about 2000%, from about 10% to about 1750%, from about 10% to about 1500%, from about 10% to about 1250%, from about 10% to about 1000%, from about 10% to about 800%, from about 10% to about 600%, from about 10% to about 500%, from about 10% to about 400%, from about 10% to about 300%, from about 10% to about 250%, from about 10% to about 200%, from about 10% to about 150%, from about 10% to about 100%, from about 10% to about 75%, from about 10% to about 50%, from about 10% to about 25%, from about 25% to about 2500%, from about 25% to about 2000%, from about 25% to about 1750%, from about 25% to about 1500%, from about 25% to about 1250%, from about 25% to about 1000%, from about 25% to about 800%, from about 25% to about 600%, from about 25% to about 500%, from about 25% to about 400%, from about 25% to about 300%, from about 25% to about 250%, from about 25% to about 200%, from about 25% to about 150%, from about 25% to about 100%, from about 25% to about 75%, from about 25% to about 50%, from about 50% to about 2500%, from about 50% to about 2000%, from about 50% to about 1750%, from about 50% to about 1500%, from about 50% to about 1250%, from about 50% to about 1000%, from about 50% to about 800%, from about 50% to about 600%, from about 50% to about 500%, from about 50% to about 400%, from about 50% to about 300%, from about 50% to about 250%, from about 50% to about 200%, from about 50% to about 150%, from about 50% to about 100%, from about 50% to about 75%, from about 75% to about 2500%, from about 75% to about 2000%, from about 75% to about 1750%, from about 75% to about 1500%, from about 75% to about 1250%, from about 75% to about 1000%, from about 75% to about 800%, from about 75% to about 600%, from about 75% to about 500%, from about 75% to about 400%, from about 75% to about 300%, from about 75% to about 250%, from about 75% to about 200%, from about 75% to about 150%, from about 75% to about 100%, from about 100% to about 2500%, from about 100% to about 2000%, from about 100% to about 1750%, from about 100% to about 1500%, from about 100% to about 1250%, from about 100% to about 1000%, from about 100% to about 800%, from about 100% to about 600%, from about 100% to about 500%, from about 100% to about 400%, from about 100% to about 300%, from about 100% to about 250%, from about 100% to about 200%, from about 100% to about 150%, from about 150% to about 2500%, from about 150% to about 2000%, from about 150% to about 1750%, from about 150% to about 1500%, from about 150% to about 1250%, from about 150% to about 1000%, from about 150% to about 800%, from about 150% to about 600%, from about 150% to about 500%, from about 150% to about 400%, from about 150% to about 300%, from about 150% to about 250%, from about 150% to about 200%, from about 200% to about 2500%, from about 200% to about 2000%, from about 200% to about 1750%, from about 200% to about 1500%, from about 200% to about 1250%, from about 200% to about 1000%, from about 200% to about 800%, from about 200% to about 600%, from about 200% to about 500%, from about 200% to about 400%, from about 200% to about 300%, from about 200% to about 250%, from about 250% to about 2500%, from about 250% to about 2000%, from about 250% to about 1750%, from about 250% to about 1500%, from about 250% to about 1250%, from about 250% to about 1000%, from about 250% to about 800%, from about 250% to about 600%, from about 250% to about 500%, from about 250% to about 400%, from about 250% to about 300%, from about 300% to about 2500%, from about 300% to about 2000%, from about 300% to about 1750%, from about 300% to about 1500%, from about 300% to about 1250%, from about 300% to about 1000%, from about 300% to about 800%, from about 300% to about 600%, from about 300% to about 500%, from about 300% to about 400%, from about 400% to about 2500%, from about 400% to about 2000%, from about 400% to about 1750%, from about 400% to about 1500%, from about 400% to about 1250%, from about 400% to about 1000%, from about 400% to about 800%, from about 400% to about 600%, from about 400% to about 500%, from about 500% to about 2500%, from about 500% to about 2000%, from about 500% to about 1750%, from about 500% to about 1500%, from about 500% to about 1250%, from about 500% to about 1000%, from about 500% to about 800%, from about 500% to about 600%, from about 600% to about 2500%, from about 600% to about 2000%, from about 600% to about 1750%, from about 600% to about 1500%, from about 600% to about 1250%, from about 600% to about 1000%, from about 600% to about 800%, from about 800% to about 2500%, from about 800% to about 2000%, from about 800% to about 1750%, from about 800% to about 1500%, from about 800% to about 1250%, from about 800% to about 1000%, from about 1000% to about 2500%, from about 1000% to about 2000%, from about 1000% to about 1750%, from about 1000% to about 1500%, from about 1000% to about 1250%, from about 1250% to about 2500%, from about 1250% to about 2000%, from about 1250% to about 1500%, from about 1500% to about 2500%, from about 1500% to about 2000%, or from about 2000% to about 2500% of a flow rate of a feedstock.

Additionally or alternatively, the stripping fluid may enter the at least one inlet chamber 2 at a pressure from about 5 psig to about 2000 psig, e.g., from about 5 psig to about 1800 psig, from about 5 psig to about 1600 psig, from about 5 psig to about 1400 psig, from about 5 psig to about 1200 psig, from about 5 psig to about 1000 psig, from about 5 psig to about 800 psig, from about 5 psig to about 600 psig, from about 5 psig to about 500 psig, from about 5 psig to about 400 psig, from about 5 psig to about 300 psig, from about 5 psig to about 200 psig, from about 5 psig to about 100 psig, from about 5 psig to about 75 psig, from about 5 psig to about 50 psig, from about 5 psig to about 25 psig, from about 5 psig to about 15 psig, from about 5 psig to about 10 psig, from about 10 psig to about 2000 psig, from about 10 psig to about 1800 psig, from about 10 psig to about 1600 psig, from about 10 psig to about 1400 psig, from about 10 psig to about 1200 psig, from about 10 psig to about 1000 psig, from about 10 psig to about 800 psig, from about 10 psig to about 600 psig, from about 10 psig to about 500 psig, from about 10 psig to about 400 psig, from about 10 psig to about 300 psig, from about 10 psig to about 200 psig, from about 10 psig to about 100 psig, from about 10 psig to about 75 psig, from about 10 psig to about 50 psig, from about 10 psig to about 25 psig, from about 10 psig to about 15 psig, from about 15 psig to about 2000 psig, from about 15 psig to about 1800 psig, from about 10 psig to about 1600 psig, from about 15 psig to about 1400 psig, from about 15 psig to about 1200 psig, from about 15 psig to about 1000 psig, from about 15 psig to about 800 psig, from about 15 psig to about 600 psig, from about 15 psig to about 500 psig, from about 15 psig to about 400 psig, from about 15 psig to about 300 psig, from about 15 psig to about 200 psig, from about 15 psig to about 100 psig, from about 15 psig to about 75 psig, from about 15 psig to about 50 psig, from about 15 psig to about 25 psig, from about 25 psig to about 2000 psig, from about 25 psig to about 1800 psig, from about 25 psig to about 1600 psig, from about 25 psig to about 1400 psig, from about 25 psig to about 1200 psig, from about 25 psig to about 1000 psig, from about 25 psig to about 800 psig, from about 25 psig to about 600 psig, from about 25 psig to about 500 psig, from about 25 psig to about 400 psig, from about 25 psig to about 300 psig, from about 25 psig to about 200 psig, from about 25 psig to about 100 psig, from about 25 psig to about 75 psig, from about 25 psig to about 50 psig, from about 50 psig to about 2000 psig, from about 50 psig to about 1800 psig, from about 50 psig to about 1600 psig, from about 50 psig to about 1400 psig, from about 50 psig to about 1200 psig, from about 50 psig to about 1000 psig, from about 50 psig to about 800 psig, from about 50 psig to about 600 psig, from about 50 psig to about 500 psig, from about 50 psig to about 400 psig, from about 50 psig to about 300 psig, from about 50 psig to about 200 psig, from about 50 psig to about 100 psig, from about 50 psig to about 75 psig, from about 75 psig to about 2000 psig, from about 75 psig to about 1800 psig, from about 75 psig to about 1600 psig, from about 75 psig to about 1400 psig, from about 75 psig to about 1200 psig, from about 75 psig to about 1000 psig, from about 75 psig to about 800 psig, from about 75 psig to about 600 psig, from about 75 psig to about 500 psig, from about 75 psig to about 400 psig, from about 75 psig to about 300 psig, from about 75 psig to about 200 psig, from about 75 psig to about 100 psig, from about 100 psig to about 2000 psig, from about 100 psig to about 1800 psig, from about 100 psig to about 1600 psig, from about 100 psig to about 1400 psig, from about 100 psig to about 1200 psig, from about 100 psig to about 1000 psig, from about 100 psig to about 800 psig, from about 100 psig to about 600 psig, from about 100 psig to about 500 psig, from about 100 psig to about 400 psig, from about 100 psig to about 300 psig, from about 100 psig to about 200 psig, from about 200 psig to about 2000 psig, from about 200 psig to about 1800 psig, from about 200 psig to about 1600 psig, from about 200 psig to about 1400 psig, from about 200 psig to about 1200 psig, from about 200 psig to about 1000 psig, from about 200 psig to about 800 psig, from about 200 psig to about 600 psig, from about 200 psig to about 500 psig, from about 200 psig to about 400 psig, from about 200 psig to about 300 psig, from about 300 psig to about 2000 psig, from about 300 psig to about 1800 psig, from about 300 psig to about 1600 psig, from about 300 psig to about 1400 psig, from about 300 psig to about 1200 psig, from about 300 psig to about 1000 psig, from about 300 psig to about 800 psig, from about 300 psig to about 600 psig, from about 300 psig to about 500 psig, from about 300 psig to about 400 psig, from about 400 psig to about 2000 psig, from about 400 psig to about 1800 psig, from about 400 psig to about 1600 psig, from about 400 psig to about 1400 psig, from about 400 psig to about 1200 psig, from about 400 psig to about 1000 psig, from about 400 psig to about 800 psig, from about 400 psig to about 600 psig, from about 400 psig to about 500 psig, from about 500 psig to about 2000 psig, from about 500 psig to about 1800 psig, from about 500 psig to about 1600 psig, from about 500 psig to about 1400 psig, from about 500 psig to about 1200 psig, from about 500 psig to about 1000 psig, from about 500 psig to about 800 psig, from about 500 psig to about 600 psig, from about 600 psig to about 2000 psig, from about 600 psig to about 1800 psig, from about 600 psig to about 1600 psig, from about 600 psig to about 1400 psig, from about 600 psig to about 1200 psig, from about 600 psig to about 1000 psig, from about 600 psig to about 800 psig, from about 800 psig to about 2000 psig, from about 800 psig to about 1800 psig, from about 800 psig to about 1600 psig, from about 800 psig to about 1400 psig, from about 800 psig to about 1200 psig, from about 800 psig to about 1000 psig, from about 1000 psig to about 2000 psig, from about 1000 psig to about 1800 psig, from about 1000 psig to about 1600 psig, from about 1000 psig to about 1400 psig, from about 1000 psig to about 1200 psig, from about 1200 psig to about 2000 psig, from about 1200 psig to about 1800 psig, from about 1200 psig to about 1600 psig, from about 1200 psig to about 1400 psig, from about 1400 psig to about 2000 psig, from about 1400 psig to about 1800 psig, from about 1400 psig to about 1600 psig, from about 1600 psig to about 2000 psig, from about 1600 psig to about 1800 psig, or from about 1800 psig to about 2000 psig. In particular, the stripping fluid can enter the at least one inlet chamber 2 at a pressure from about 15 psig to about 1500 psig.

G. Wall

Additionally or alternatively, a multiphase separator 1 may further comprise at least one wall 10. The at least one wall 10 may be generally disposed on at least a portion of an exterior surface of the at least one stripping chamber 4, wherein the at least one wall 10 can guide the stripping fluid into the perforations 7 of the at least one stripping chamber 4 and can advantageously also prevent the stripping fluid from flowing directly into the at least one collection chamber 8.

Additionally or alternatively, the at least one wall 10 may include multiple walls 10, e.g., at least two walls 10, at least three walls 10, at least four walls 10, at least five walls 10, at least six walls 10, at least seven walls 10, at least eight walls 10, at least nine walls 10, at least ten walls 10, at least twelve walls 10, at least fourteen walls 10, at least sixteen walls 10, at least eighteen walls 10, at least twenty walls 10, etc. In particular, a multiphase separator 1 can comprise at least two walls 10, wherein each wall may be generally disposed on at least a portion of an exterior surface of the least one stripping chamber 4.

In various aspects, a multiphase separator 1 may comprise at least one stripping chamber 4, which may include at least a first stripping chamber 4 and a second stripping chamber 4, wherein the at least one wall 10 may be generally disposed in between the first stripping chamber 4 and the second stripping chamber 4. When the at least one stripping chamber 4 includes multiple stripping chambers 4, at least one wall 10 may or may not be present. If present, the at least one wall 10 may be generally disposed between each of the multiple stripping chambers 4.

III. Process for Producing a Hydrocarbon Product

In another embodiment, a process for converting a feedstock to a hydrocarbon product is provided A. Feedstock In the process, a feedstock and a catalyst are fed to a reaction zone of at least one reactor, wherein the feedstock and the catalyst travel through the at least one reactor under conditions to produce a mixture (e.g., three-phase) comprising converted hydrocarbon product, unconverted feedstock, and/or spent catalyst. The feedstock and unconverted feedstock may be in a single phase (e.g., gas or liquid) or may be in a mixed phase (e.g., gas and liquid). Additionally, the feedstock and the unconverted feedstock may comprise various oxygenates and/or olefins.

The oxygenates may include, but are not limited to, alcohols, ethers, carbonyl compounds, e.g., aldehydes, ketones and carboxylic acids, and mixtures thereof. In particular, the oxygenate feedstock comprises $C_1$-$C_4$ mono-alcohols (e.g., methanol, ethanol, propanol, butanol, etc.), di-alcohols, polyols, dimethyl ether (DME) or a mixture thereof. The methanol can be obtained from coal, natural gas and biomass by conventional processes. Additionally or alternatively, the feedstock may include water. For example, the methanol can be obtained from coal with a water content up to about 10%, particularly from about 5.0 to about 10%; and/or from natural gas with a water content up to about 40%, particularly from about 20% to about 40%, from about 30% to about 40%, or from about 20% to about 30%.

The amount of oxygenate in the feedstock may be from about 10 wt % to about 100 wt %, e.g., from about 10 wt % to about 99.5 wt %, from about 10 wt % to about 99 wt %, from about 10 wt % to about 95 wt %, from about 10 wt % to about 90 wt %, from about 10 wt % to about 85 wt %, from about 10 wt % to about 80 wt %, from about 10 wt % to about 75 wt %, from about 10 wt % to about 70 wt %, from about 10 wt % to about 65 wt %, from about 10 wt % to about 60 wt %, from about 10 wt % to about 55 wt %, from about 10 wt % to about 50 wt %, from about 10 wt % to about 45 wt %, from about 10 wt % to about 40 wt %, from about 10 wt % to about 35 wt %, from about 10 wt % to about 30 wt %, from about 10 wt % to about 25 wt %, from about 10 wt % to about 20 wt %, from about 10 wt % to about 15 wt %, from about 15 wt % to about 100 wt %, from about 15 wt % to about 99.5 wt %, from about 15 wt % to about 99 wt %, from about 15 wt % to about 95 wt %, from about 15 wt % to about 90 wt %, from about 15 wt % to about 85 wt %, from about 15 wt % to about 80 wt %, from about 15 wt % to about 75 wt %, from about 15 wt % to about 70 wt %, from about 15 wt % to about 65 wt %, from about 15 wt % to about 60 wt %, from about 15 wt % to about 55 wt %, from about 15 wt % to about 50 wt %, from about 15 wt % to about 45 wt %, from about 15 wt % to about 40 wt %, from about 15 wt % to about 35 wt %, from about 15 wt % to about 30 wt %, from about 10 wt % to about 25 wt %, from about 15 wt % to about 20 wt %, from about 20 wt % to about 100 wt %, from about 20 wt % to about 99.5 wt %, from about 20 wt % to about 99 wt %, from about 20 wt % to about 95 wt %, from about 20 wt % to about 90 wt %, from about 20 wt % to about 85 wt %, from about 20 wt % to about 80 wt %, from about 20 wt % to about 75 wt %, from about 20 wt % to about 70 wt %, from about 20 wt % to about 65 wt %, from about 20 wt % to about 60 wt %, from about 20 wt % to about 55 wt %, from about 20 wt % to about 50 wt %, from about 20 wt % to about 45 wt %, from about 20 wt % to about 40 wt %, from about 20 wt % to about 35 wt %, from about 20 wt % to about 30 wt %, from about 20 wt % to about 25 wt %, from about 25 wt % to about 100 wt %, from about 25 wt % to about 99.5 wt %, from about 25 wt % to about 99 wt %, from about 25 wt % to about 95 wt %, from about 25 wt % to about 90 wt %, from about 25 wt % to about 85 wt %, from about 25 wt % to about 80 wt %, from about 25 wt % to about 75 wt %, from about 25 wt % to about 70 wt %, from about 25 wt % to about 65 wt %, from about 25 wt % to about 60 wt %, from about 25 wt % to about 55 wt %, from about 25 wt % to about 50 wt %, from about 25 wt % to about 45 wt %, from about 25 wt % to about 40 wt %, from about 25 wt % to about 35 wt %, from about 25 wt % to about 30 wt %, from about 30 wt % to about 100 wt %, from about 30 wt % to about 99.5 wt %, from about 30 wt % to about 99 wt %, from about 30 wt % to about 95 wt %, from about 30 wt % to about 90 wt %, from about 30 wt % to about 85 wt %, from about 30 wt % to about 80 wt %, from about 30 wt % to about 75 wt %, from about 30 wt % to about 70 wt %, from about 30 wt % to about 65 wt %, from about 30 wt % to about 60 wt %, from about 30 wt % to about 55 wt %, from about 30 wt % to about 50 wt %, from about 30 wt % to about 45 wt %, from about 30 wt % to about 40 wt %, from about 30 wt % to about 35 wt %, from about 35 wt % to about 100 wt %, from about 35 wt % to about 99.5 wt %, from about 35 wt % to about 99 wt %, from about 35 wt % to about 95 wt %, from about 35 wt % to about 90 wt %, from about 35 wt % to about 85 wt %, from about 35 wt % to about 80 wt %, from about 35 wt % to about 75 wt %, from about 35 wt % to about 70 wt %, from about 35 wt % to about 65 wt %, from about 35 wt % to about 60 wt %, from about 35 wt % to about 55 wt %, from about 35 wt % to about 50 wt %, from about 35 wt % to about 45 wt %, from about 35 wt % to about 40 wt %, from about 40 wt % to about 100 wt %, from about 40 wt % to about 99.5 wt %, from about 40 wt % to about 99 wt %, from about 40 wt % to about 95 wt %, from about 40 wt % to about 90 wt %, from about 40 wt % to about 85 wt %, from about 40 wt % to about 80 wt %, from about 40 wt % to about 75 wt %, from about 40 wt % to about 70 wt %, from about 40 wt % to about 65 wt %, from about 40 wt % to about 60 wt %, from about 40 wt % to about 55 wt %, from about 40 wt % to about 50 wt %, from about 40 wt % to about 45 wt %, from about 45 wt % to about 100 wt %, from about 45 wt % to about 99.5 wt %, from about 45 wt % to about 99 wt %, from about 45 wt % to about 95 wt %, from about 45 wt % to about 90 wt %, from about 45 wt % to about 85 wt %, from about 45 wt % to about 80 wt %, from about 45 wt % to about 75 wt %, from about 45 wt % to about 70 wt %, from about 45 wt % to about 65 wt %, from about 45 wt % to about 60 wt %, from about 45 wt % to about 55 wt %, from about 45 wt % to about 50 wt %, from about 50 wt % to about 100 wt %, from about 50 wt % to about 99.5 wt %, from about 50 wt % to about 99 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 65 wt %, from about 50 wt % to about 60 wt %, from about 50 wt % to about 55 wt %, from about 55 wt % to about 100 wt % to about 99.5 wt %, from about 55 wt % to about 99 wt %, from about 55 wt % to about 95 wt %, from about 55 wt % to about 90 wt %, from about 55 wt % to about 85 wt %, from about 55 wt % to about 80 wt %, from about 55 wt % to about 75 wt %, from about 55 wt % to about 70 wt %, from about 55 wt % to about 65 wt %, from about 55 wt % to about 60 wt %, from about 60 wt % to about 100 wt %, from about 60 wt % to about 99.5 wt %, from about 60 wt % to about 99 wt %, from about 60 wt % to about 95 wt %, from about 60 wt % to about 90 wt %, from about 60 wt % to about 85 wt %, from about 60 wt % to about 80 wt %, from about 60 wt % to about 75 wt %, from about 60 wt % to about 70 wt %, from about 60 wt % to about 65 wt %, from about 65 wt % to about 100 wt %, from about 65 wt % to about 99.5 wt %, from about 65 wt % to about 99 wt %, from about 65 wt % to about 95 wt %, from about 65 wt % to about 90 wt %, from about 65 wt % to about 85 wt %, from about 65 wt % to about 80 wt %, from about 65 wt % to about 75 wt %, from about 65 wt % to about 70 wt %, from about 70 wt % to about 100 wt %, from about 70 wt % to about 99.5 wt %, from about 70 wt % to about 99 wt %, from about 70 wt % to about 95 wt %, from about 70 wt % to about 90 wt %, from about 70 wt % to about 85 wt %, from about 70 wt % to about 80 wt %, from about 70 wt % to about 75 wt %, from about 75 wt % to about 100 wt %, from about 75 wt % to about 99.5 wt %, from about 75 wt % to about 99 wt %, from about 75 wt % to about 95 wt %, from about 75 wt % to about 90 wt %, from about 75 wt % to about 85 wt %, from about 75 wt % to about 80 wt %, from about 80 wt % to about 100 wt %, from about 80 wt % to about 99.5 wt %, from about 80 wt % to about 95 wt %, from about 80 wt % to about 90 wt %, from about 80 wt % to about 85 wt %, from about 85 wt % to about 100 wt %, from about 85 wt % to about 99.5 wt %, from about 85 wt % to about 95 wt %, from about 85 wt % to about 90 wt %, from about 90 wt % to about 100 wt %, from about 90 wt % to about 99.5 wt %, from about 90 wt % to about 95 wt %, from about 95 wt % to about 100 wt %, from about 95 wt % to about 99.5 wt %, or from about 99.5 wt % to about 100 wt %.

Any olefins present in the feedstock may have 2 to 20 carbons atoms, particularly 2 to 16 carbon atoms, 3 to 9 carbon atoms, or 2 to 5 carbon atoms. In particular, the olefins may comprise $C_{2+}$ olefins. Examples of olefins that may be present in the feedstock include, but are not limited to ethylene, propylenes, butylenes (e.g., 1-butene, 3-methyl-1-butene,), pentylenes (e.g., 4-methyl-1-pentene, 3-methyl-1-pentene), octylenes (e.g., 1-octene), hexylenes (e.g., 1-hexene), and the like, as well as combinations thereof.

The amount of olefins in the feedstock may be from about 10 wt % to about 100 wt %, e.g., from about 10 wt % to about 99.5 wt %, from about 10 wt % to about 99 wt %, from about 10 wt % to about 95 wt %, from about 10 wt % to about 90 wt %, from about 10 wt % to about 85 wt %, from about 10 wt % to about 80 wt %, from about 10 wt % to about 75 wt %, from about 10 wt % to about 70 wt %, from about 10 wt % to about 65 wt %, from about 10 wt % to about 60 wt %, from about 10 wt % to about 55 wt %, from about 10 wt % to about 50 wt %, from about 10 wt % to about 45 wt %, from about 10 wt % to about 40 wt %, from about 10 wt % to about 35 wt %, from about 10 wt % to about 30 wt %, from about 10 wt % to about 25 wt %, from about 10 wt % to about 20 wt %, from about 10 wt % to about 15 wt %, from about 15 wt % to about 100 wt %, from about 15 wt % to about 99.5 wt %, from about 15 wt % to about 99 wt %, from about 15 wt % to about 95 wt %, from about 15 wt % to about 90 wt %, from about 15 wt % to about 85 wt %, from about 15 wt % to about 80 wt %, from about 15 wt % to about 75 wt %, from about 15 wt % to about 70 wt %, from about 15 wt % to about 65 wt %, from about 15 wt % to about 60 wt %, from about 15 wt % to about 55 wt %, from about 15 wt % to about 50 wt %, from about 15 wt % to about 45 wt %, from about 15 wt % to about 40 wt %, from about 15 wt % to about 35 wt %, from about 15 wt % to about 30 wt %, from about 10 wt % to about 25 wt %, from about 15 wt % to about 20 wt %, from about 20 wt % to about 100 wt %, from about 20 wt % to about 99.5 wt %, from about 20 wt % to about 99 wt %, from about 20 wt % to about 95 wt %, from about 20 wt % to about 90 wt %, from about 20 wt % to about 85 wt %, from about 20 wt % to about 80 wt %, from about 20 wt % to about 75 wt %, from about 20 wt % to about 70 wt %, from about 20 wt % to about 65 wt %, from about 20 wt % to about 60 wt %, from about 20 wt % to about 55 wt %, from about 20 wt % to about 50 wt %, from about 20 wt % to about 45 wt %, from about 20 wt % to about 40 wt %, from about 20 wt % to about 35 wt %, from about 20 wt % to about 30 wt %, from about 20 wt % to about 25 wt %, from about 25 wt % to about 100 wt %, from about 25 wt % to about 99.5 wt %, from about 25 wt % to about 99 wt %, from about 25 wt % to about 95 wt %, from about 25 wt % to about 90 wt %, from about 25 wt % to about 85 wt %, from about 25 wt % to about 80 wt %, from about 25 wt % to about 75 wt %, from about 25 wt % to about 70 wt %, from about 25 wt % to about 65 wt %, from about 25 wt % to about 60 wt %, from about 25 wt % to about 55 wt %, from about 25 wt % to about 50 wt %, from about 25 wt % to about 45 wt %, from about 25 wt % to about 40 wt %, from about 25 wt % to about 35 wt %, from about 25 wt % to about 30 wt %, from about 30 wt % to about 100 wt %, from about 30 wt % to about 99.5 wt %, from about 30 wt % to about 99 wt %, from about 30 wt % to about 95 wt %, from about 30 wt % to about 90 wt %, from about 30 wt % to about 85 wt %, from about 30 wt % to about 80 wt %, from about 30 wt % to about 75 wt %, from about 30 wt % to about 70 wt %, from about 30 wt % to about 65 wt %, from about 30 wt % to about 60 wt %, from about 30 wt % to about 55 wt %, from about 30 wt % to about 50 wt %, from about 30 wt % to about 45 wt %, from about 30 wt % to about 40 wt %, from about 30 wt % to about 35 wt %, from about 35 wt % to about 100 wt %, from about 35 wt % to about 99.5 wt %, from about 35 wt % to about 99 wt %, from about 35 wt % to about 95 wt %, from about 35 wt % to about 90 wt %, from about 35 wt % to about 85 wt %, from about 35 wt % to about 80 wt %, from about 35 wt % to about 75 wt %, from about 35 wt % to about 70 wt %, from about 35 wt % to about 65 wt %, from about 35 wt % to about 60 wt %, from about 35 wt % to about 55 wt %, from about 35 wt % to about 50 wt %, from about 35 wt % to about 45 wt %, from about 35 wt % to about 40 wt %, from about 40 wt % to about 100 wt %, from about 40 wt % to about 99.5 wt %, from about 40 wt % to about 99 wt %, from about 40 wt % to about 95 wt %, from about 40 wt % to about 90 wt %, from about 40 wt % to about 85 wt %, from about 40 wt % to about 80 wt %, from about 40 wt % to about 75 wt %, from about 40 wt % to about 70 wt %, from about 40 wt % to about 65 wt %, from about 40 wt % to about 60 wt %, from about 40 wt % to about 55 wt %, from about 40 wt % to about 50 wt %, from about 45 wt % to about 100 wt %, from about 45 wt % to about 99.5 wt %, from about 45 wt % to about 99 wt %, from about 45 wt % to about 95 wt %, from about 45 wt % to about 90 wt %, from about 45 wt % to about 85 wt %, from about 45 wt % to about 80 wt %, from about 45 wt % to about 75 wt %, from about 45 wt % to about 70 wt %, from about 45 wt % to about 65 wt %, from about 45 wt % to about 60 wt %, from about 45 wt % to about 55 wt %, from about 45 wt % to about 50 wt %, from about 50 wt % to about 100 wt %, from about 50 wt % to about 99.5 wt %, from about 50 wt % to about 99 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 65 wt %, from about 50 wt % to about 60 wt %, from about 50 wt % to about 55 wt %, from about 55 wt % to about 100 wt %, from about 55 wt % to about 99.5 wt %, from about 55 wt % to about 99 wt %, from about 55 wt % to about 95 wt %, from about 55 wt % to about 90 wt %, from about 55 wt % to about 85 wt %, from about 55 wt % to about 80 wt %, from about 55 wt % to about 75 wt %, from about 55 wt % to about 70 wt %, from about 55 wt % to about 65 wt %, from about 55 wt % to about 60 wt %, from about 60 wt % to about 100 wt %, from about 60 wt % to about 99.5 wt %, from about 60 wt % to about 99 wt %, from about 60 wt % to about 95 wt %, from about 60 wt % to about 90 wt %, from about 60 wt % to about 85 wt %, from about 60 wt % to about 80 wt %, from about 60 wt % to about 75 wt %, from about 60 wt % to about 70 wt %, from about 60 wt % to about 65 wt %, from about 65 wt % to about 100 wt %, from about 65 wt % to about 99.5 wt %, from about 65 wt % to about 99 wt %, from about 65 wt % to about 95 wt %, from about 65 wt % to about 90 wt %, from about 65 wt % to about 85 wt %, from about 65 wt % to about 80 wt %, from about 65 wt % to about 75 wt %, from about 65 wt % to about 70 wt %, from about 70 wt % to about 100 wt %, from about 70 wt % to about 99.5 wt %, from about 70 wt % to about 99 wt %, from about 70 wt % to about 95 wt %, from about 70 wt % to about 90 wt %, from about 70 wt % to about 85 wt %, from about 70 wt % to about 80 wt %, from about 70 wt % to about 75 wt %, from about 75 wt % to about 100 wt %, from about 75 wt % to about 99.5 wt %, from about 75 wt % to about 99 wt %, from about 75 wt % to about 95 wt %, from about 75 wt % to about 90 wt %, from about 75 wt % to about 85 wt %, from about 75 wt % to about 80 wt %, from about 80 wt % to about 100 wt %, from about 80 wt % to about 99.5 wt %, from about 80 wt % to about 95 wt %, from about 80 wt % to about 90 wt %, from about 80 wt % to about 85 wt %, from about 85 wt % to about 100 wt %, from about 85 wt % to about 99.5 wt %, from about 85 wt % to about 95 wt %, from about 85 wt % to about 90 wt %, from about 90 wt % to about 100 wt %, from about 90 wt % to about 99.5 wt %, from about 90 wt % to about 95 wt %, from about 95 wt % to about 100 wt %, from about 95 wt % to about 99.5 wt %, or from about 99.5 wt % to about 100 wt %.

Additionally or alternatively, one or more other compounds may be present in the feedstock. The other compounds may have 1 to about 50 carbon atoms, e.g., 1 to about 20 carbon atoms, 1 to about 10 carbon atoms, or 1 to about 4 carbon atoms. Such other compounds may include or be paraffins. Typically, although not necessarily, such other compounds include one or more heteroatoms other than oxygen, including but not limited to amines, halides, mercaptans, sulfides, and the like. Particularly, such compounds include alkyl-mercaptans (e.g., methyl mercaptan and ethyl mercaptan), alkyl-sulfides (e.g., methyl sulfide), alkyl-amines (e.g., methyl amine), and alkyl-halides (e.g., methyl chloride and ethyl chloride). Additionally, such other compounds may include or be inert gases (e.g., $N_2$) and/or water. The amount of such other compounds in the feedstock may be from about 2.0 wt % to about 95 wt %, e.g., from about 2.0 wt % to about 90 wt %, from about 2.0 wt % to about 75 wt %, from about 2.0 wt % to about 60 wt %, from about 2.0 wt % to about 50 wt %, from about 2.0 wt % to about 45 wt %, from about 2.0 wt % to about 40 wt %, from about 2.0 wt % to about 35 wt %, from about 2.0 wt % to about 30 wt %, from about 2.0 wt % to about 25 wt %, from about 2.0 wt % to about 20 wt %, from about 2.0 wt % to about 15 wt %, from about 2.0 wt % to about 10 wt %, from about 2.0 wt % to about 5.0 wt %, from about 5.0 wt % to about 95 wt %, from about 5.0 wt % to about 90 wt %, from about 5.0 wt % to about 75 wt %, from about 5.0 wt % to about 60 wt %, from about 5.0 wt % to about 50 wt %, from about 5.0 wt % to about 45 wt %, from about 5.0 wt % to about 40 wt %, from about 5.0 wt % to about 35 wt %, from about 5.0 wt % to about 30 wt %, from about 5.0 wt % to about 25 wt %, from about 5.0 wt % to about 20 wt %, from about 5.0 wt % to about 15 wt %, from about 5.0 wt % to about 10 wt %, from about 10 wt % to about 95 wt %, from about 10 wt % to about 90 wt %, from about 10 wt % to about 75 wt %, from about 10 wt % to about 60 wt %, from about 10 wt % to about 50 wt %, from about 10 wt % to about 45 wt %, from about 10 wt % to about 40 wt %, from about 10 wt % to about 35 wt %, from about 10 wt % to about 30 wt %, from about 10 wt % to about 25 wt %, from about 10 wt % to about 20 wt %, from about 10 wt % to about 15 wt %, from about 20 wt % to about 95 wt %, from about 20 wt % to about 90 wt %, from about 20 wt % to about 75 wt %, from about 20 wt % to about 60 wt %, from about 20 wt % to about 50 wt %, from about 20 wt % to about 45 wt %, from about 20 wt % to about 40 wt %, from about 20 wt % to about 35 wt %, from about 20 wt % to about 30 wt %, from about 20 wt % to about 25 wt %, from about 25 wt % to about 95 wt %, from about 25 wt % to about 90 wt %, from about 25 wt % to about 75 wt %, from about 25 wt % to about 60 wt %, from about 25 wt % to about 50 wt %, from about 25 wt % to about 45 wt %, from about 25 wt % to about 40 wt %, from about 25 wt % to about 35 wt %, from about 25 wt % to about 30 wt %, from about 30 wt % to about 95 wt %, from about 30 wt % to about 90 wt %, from about 30 wt % to about 75 wt %, from about 30 wt % to about 60 wt %, from about 30 wt % to about 50 wt %, from about 30 wt % to about 45 wt %, from about 30 wt % to about 40 wt %, from about 30 wt % to about 35 wt %, from about 40 wt % to about 95 wt %, from about 40 wt % to about 90 wt %, from about 40 wt % to about 75 wt %, from about 40 wt % to about 60 wt %, from about 40 wt % to about 50 wt %, from about 40 wt % to about 45 wt %, from about 45 wt % to about 95 wt %, from about 45 wt % to about 90 wt %, from about 45 wt % to about 75 wt %, from about 45 wt % to about 60 wt %, from about 50 wt % to about 95 wt %, from about 50 wt % to about 90 wt %, from about 50 wt % to about 75 wt %, from about 50 wt % to about 60 wt %, from about 60 wt % to about 95 wt %, from about 60 wt % to about 90 wt %, from about 60 wt % to about 75 wt %, from about 75 wt % to about 95 wt %, from about 75 wt % to about 90 wt %, or from about 90 wt % to about 95 wt %.

Additionally or alternatively, the oxygenate (e.g., methanol) in the feedstock has a conversion (wt/wt) to the hydrocarbon product from about 30% to about 100%, e.g., from about 30% to about 99.5%, from about 30% to about 99%, from about 30% to about 95%, from about 30% to about 90%, from about 30% to about 85%, from about 30% to about 80%, from about 30% to about 75%, from about 30% to about 70%, from about 30% to about 65%, from about 30% to about 60%, from about 30% to about 55%, from about 30% to about 50%, from about 30% to about 45%, from about 30% to about 40%, from about 30% to about 35%, from about 35% to about 100%, from about 35% to about 99.5%, from about 35% to about 99%, from about 35% to about 95%, from about 35% to about 90%, from about 35% to about 85%, from about 35% to about 80%, from about 35% to about 75%, from about 35% to about 70%, from about 35% to about 65%, from about 35% to about 60%, from about 35% to about 55%, from about 35% to about 50%, from about 35% to about 45%, from about 35% to about 40%, from about 40% to about 100%, from about 40% to about 99.5%, from about 40% to about 99%, from about 40% to about 95%, from about 40% to about 90%, from about 40% to about 85%, from about 40% to about 80%, from about 40% to about 75%, from about 40% to about 70%, from about 40% to about 65%, from about 40% to about 60%, from about 40% to about 55%, from about 40% to about 50%, from about 40% to about 45%, from about 45% to about 100%, from about 45% to about 99.5%, from about 45% to about 99%, from about 45% to about 95%, from about 45% to about 90%, from about 45% to about 85%, from about 45% to about 80%, from about 45% to about 75%, from about 45% to about 70%, from about 45% to about 65%, from about 45% to about 60%, from about 45% to about 55%, from about 45% to about 50%, from about 50% to about 100%, from about 50% to about 99.5%, from about 50% to about 99%, from about 50% to about 95%, from about 50% to about 90%, from about 50% to about 85%, from about 50% to about 80%, from about 50% to about 75%, from about 50% to about 70%, from about 50% to about 65%, from about 50% to about 60%, from about 50% to about 55%, from about 55% to about 100%, from about 55% to about 99.5%, from about 55% to about 99%, from about 55% to about 95%, from about 55% to about 90%, from about 55% to about 85%, from about 55% to about 80%, from about 55% to about 75%, from about 55% to about 70%, from about 55% to about 65%, from about 55% to about 60%, from about 60% to about 100%, from about 60% to about 99.5%, from about 60% to about 99%, from about 60% to about 95%, from about 60% to about 90%, from about 60% to about 85%, from about 60% to about 80%, from about 60% to about 75%, from about 60% to about 70%, from about 60% to about 65%, from about 65% to about 100%, from about 65% to about 99.5%, from about 65% to about 99%, from about 65% to about 95%, from about 65% to about 90%, from about 65% to about 85%, from about 65% to about 80%, from about 65% to about 75%, from about 65% to about 70%, from about 70% to about 100%, from about 70% to about 99.5%, from about 70% to about 99%, from about 70% to about 95%, from about 70% to about 90%, from about 70% to about 85%, from about 70% to about 80%, from about 70% to about 75%, from about 75% to about 100%, from about 75% to about 99.5%, from about 75% to about 99%, from about 75% to about 95%, from about 75% to about 90%, from about 75% to about 85%, from about 75% to about 80%, from about 80% to about 100%, from about 80% to about 99.5%, from about 80% to about 95%, from about 80% to about 90%, from about 80% to about 85%, from about 85% to about 100%, from about 85% to about 99.5%, from about 85% to about 95%, from about 85% to about 90%, from about 90% to about 100%, from about 90% to about 99.5%, from about 90% to about 95%, from about 95% to about 100%, from about 95% to about 99.5%, or from about 99.5% to about 100%.

Additionally or alternatively, the feedstock, particularly where the feedstock comprises an alcohol (e.g., methanol), may optionally be pre-treated, e.g., to form dialkyl ether in the feedstock. For example, the feedstock may be fed to a condensation apparatus for the feedstock, e.g., for catalytic ether formation over e.g., γ-alumina, prior to introduction into the reactor. Further, optionally, at least a portion of any methanol and/or water remaining in the feedstock after catalytic dehydration may be separated from the feedstock. If desired, such catalytic reaction may be used to alter the content of reactor effluent before it enters a subsequent reactor or reaction zone.

B. Reactor

The feedstock can be fed into a reaction zone of at least one reactor, such as a moving bed reactor. Where the reactor includes more than one reactor, the reactors may be arranged in any suitable configuration, e.g., in series, parallel, or series-parallel.

The reactor can be operated under reaction conditions sufficient to convert the feedstock to a hydrocarbon product (e.g., $C_2$-$C_{22}$ hydrocarbon product). In particular, the reactor can be operated at a weight hourly space velocity (WHSV, g feedstock/g catalyst/hour) in the range from about 0.1 $hr^{-1}$ to about 2 hr$^{-1}$, e.g., from about 0.1 hr$^{-1}$ to about 2.0 hr$^{-1}$, from about 0.1 hr$^{-1}$ to about 1.5 hr$^{-1}$, from about 0.1 hr$^{-1}$ to about 1.0 hr$^{-1}$, from about 0.5 hr$^{-1}$ to about 2.0 hr$^{-1}$, from about 0.5 hr$^{-1}$ to about 1.5 hr$^{-1}$, from about 0.5 hr$^{-1}$ to about 1.0 hr$^{-1}$, from about 1.0 hr$^{-1}$ to about 2.0 hr$^{-1}$ or from about 1.0 hr$^{-1}$ to about 1.5 hr$^{-1}$.

Additionally or alternatively, temperature in the reaction zone may be from about 100° C. to about 900° C., e.g., from about 100° C. to about 850° C., from about 100° C. to about 800° C., from about 100° C. to about 750° C., from about 100° C. to about 700° C., from about 100° C. to about 650° C., from about 100° C. to about 600° C., from about 100° C. to about 550° C., from about 100° C. to about 500° C., from about 100° C. to about 450° C., from about 100° C. to about 400° C., from about 100° C. to about 350° C., from about 100° C. to about 300° C., from about 100° C. to about 250° C., from about 100° C. to about 200° C., from about 100° C. to about 150° C., from about 150° C. to about 900° C., from about 150° C. to about 850° C., from about 150° C. to about 800° C., from about 150° C. to about 750° C., from about 150° C. to about 700° C., from about 150° C. to about 650° C., from about 150° C. to about 600° C., from about 150° C. to about 550° C., from about 150° C. to about 500° C., from about 150° C. to about 450° C., from about 150° C. to about 400° C., from about 150° C. to about 350° C., from about 150° C. to about 300° C., from about 150° C. to about 250° C., from about 150° C. to about 200° C., from about 200° C. to about 900° C., from about 200° C. to about 850° C., from about 200° C. to about 800° C., from about 200° C. to about 750° C., from about 200° C. to about 700° C., from about 200° C. to about 650° C., from about 200° C. to about 600° C., from about 200° C. to about 550° C., from about 200° C. to about 500° C., from about 200° C. to about 450° C., from about 200° C. to about 400° C., from about 200° C. to about 350° C., from about 200° C. to about 300° C., from about 200° C. to about 250° C., from about 250° C. to about 900° C., from about 250° C. to about 850° C., from about 250° C. to about 800° C., from about 250° C. to about 750° C., from about 250° C. to about 700° C., from about 250° C. to about 650° C., from about 250° C. to about 600° C., from about 250° C. to about 550° C., from about 250° C. to about 500° C., from about 250° C. to about 450° C., from about 250° C. to about 400° C., from about 250° C. to about 350° C., from about 250° C. to about 300° C., from about 300° C. to about 900° C., from about 300° C. to about 850° C., from about 300° C. to about 800° C., from about 300° C. to about 750° C., from about 300° C. to about 700° C., from about 300° C. to about 650° C., from about 300° C. to about 600° C., from about 300° C. to about 550° C., from about 300° C. to about 500° C., from about 300° C. to about 450° C., from about 300° C. to about 400° C., from about 300° C. to about 350° C., from about 350° C. to about 900° C., from about 350° C. to about 850° C., from about 350° C. to about 800° C., from about 350° C. to about 750° C., from about 350° C. to about 700° C., from about 350° C. to about 650° C., from about 350° C. to about 600° C., from about 350° C. to about 550° C., from about 350° C. to about 500° C., from about 350° C. to about 450° C., from about 350° C. to about 400° C., from about 400° C. to about 900° C., from about 400° C. to about 850° C., from about 400° C. to about 800° C., from about 150° C. to about 750° C., from about 400° C. to about 700° C., from about 400° C. to about 650° C., from about 400° C. to about 600° C., from about 400° C. to about 550° C., from about 400° C. to about 500° C., from about 400° C. to about 450° C., from about 450° C. to about 900° C., from about 450° C. to about 850° C., from about 450° C. to about 800° C., from about 450° C. to about 750° C., from about 450° C. to about 700° C., from about 450° C. to about 650° C., from about 450° C. to about 600° C., from about 450° C. to about 550° C., from about 450° C. to about 500° C., from about 500° C. to about 900° C., from about 500° C. to about 850° C., from about 500° C. to about 800° C., from about 500° C. to about 750° C., from about 500° C. to about 700° C., from about 500° C. to about 650° C., from about 500° C. to about 600° C., from about 500° C. to about 550° C., from about 550° C. to about 900° C., from about 550° C. to about 850° C., from about 550° C. to about 800° C., from about 550° C. to about 750° C., from about 550° C. to about 700° C., from about 550° C. to about 650° C., from about 550° C. to about 600° C., from about 600° C. to about 900° C., from about 600° C. to about 850° C., from about 600° C. to about 800° C., from about 600° C. to about 750° C., from about 600° C. to about 700° C., from about 600° C. to about 650° C., from about 650° C. to about 900° C., from about 650° C. to about 850° C., from about 650° C. to about 800° C., from about 650° C. to about 750° C., from about 650° C. to about 700° C., from about 700° C. to about 900° C., from about 700° C. to about 850° C., from about 700° C. to about 800° C., from about 700° C. to about 750° C., from about 750° C. to about 900° C., from about 750° C. to about 850° C., from about 750° C. to about 800° C., from about 800° C. to about 900° C., from about 800° C. to about 850° C., or from about 850° C. to about 900° C. In particular, the temperature in the reactor can be from about 200° C. to about 500° C.

The above temperatures may be used in combination with a pressure in the reaction zone from about 5 psig to about 2000 psig, e.g., from about 5 psig to about 1800 psig, from about 5 psig to about 1600 psig, from about 5 psig to about 1400 psig, from about 5 psig to about 1200 psig, from about 5 psig to about 1000 psig, from about 5 psig to about 800 psig, from about 5 psig to about 600 psig, from about 5 psig to about 500 psig, from about 5 psig to about 400 psig, from about 5 psig to about 300 psig, from about 5 psig to about 200 psig, from about 5 psig to about 100 psig, from about 5 psig to about 75 psig, from about 5 psig to about 50 psig, from about 5 psig to about 25 psig, from about 5 psig to about 15 psig, from about 5 psig to about 10 psig, from about 10 psig to about 2000 psig, from about 10 psig to about 1800 psig, from about 10 psig to about 1600 psig, from about 10 psig to about 1400 psig, from about 10 psig to about 1200 psig, from about 10 psig to about 1000 psig, from about 10 psig to about 800 psig, from about 10 psig to about 600 psig, from about 10 psig to about 500 psig, from about 10 psig to about 400 psig, from about 10 psig to about 300 psig, from about 10 psig to about 200 psig, from about 10 psig to about 100 psig, from about 10 psig to about 75 psig, from about 10 psig to about 50 psig, from about 10 psig to about 25 psig, from about 10 psig to about 15 psig, from about 15 psig to about 2000 psig, from about 15 psig to about 1800 psig, from about 10 psig to about 1600 psig, from about 15 psig to about 1400 psig, from about 15 psig to about 1200 psig, from about 15 psig to about 1000 psig, from about 15 psig to about 800 psig, from about 15 psig to about 600 psig, from about 15 psig to about 500 psig, from about 15 psig to about 400 psig, from about 15 psig to about 300 psig, from about 15 psig to about 200 psig, from about 15 psig to about 100 psig, from about 15 psig to about 75 psig, from about 15 psig to about 50 psig, from about 15 psig to about 25 psig, from about 25 psig to about 2000 psig, from about 25 psig to about 1800 psig, from about 25 psig to about 1600 psig, from about 25 psig to about 1400 psig, from about 25 psig to about 1200 psig, from about 25 psig to about 1000 psig, from about 25 psig to about 800 psig, from about 25 psig to about 600 psig, from about 25 psig to about 500 psig, from about 25 psig to about 400 psig, from about 25 psig to about 300 psig, from about 25 psig to about 200 psig, from about 25 psig to about 100 psig, from about 25 psig to about 75 psig, from about 25 psig to about 50 psig, from about 50 psig to about 2000 psig, from about 50 psig to about 1800 psig, from about 50 psig to about 1600 psig, from about 50 psig to about 1400 psig, from about 50 psig to about 1200 psig, from about 50 psig to about 1000 psig, from about 50 psig to about 800 psig, from about 50 psig to about 600 psig, from about 50 psig to about 500 psig, from about 50 psig to about 400 psig, from about 50 psig to about 300 psig, from about 50 psig to about 200 psig, from about 50 psig to about 100 psig, from about 50 psig to about 75 psig, from about 75 psig to about 2000 psig, from about 75 psig to about 1800 psig, from about 75 psig to about 1600 psig, from about 75 psig to about 1400 psig, from about 75 psig to about 1200 psig, from about 75 psig to about 1000 psig, from about 75 psig to about 800 psig, from about 75 psig to about 600 psig, from about 75 psig to about 500 psig, from about 75 psig to about 400 psig, from about 75 psig to about 300 psig, from about 75 psig to about 200 psig, from about 75 psig to about 100 psig, from about 100 psig to about 2000 psig, from about 100 psig to about 1800 psig, from about 100 psig to about 1600 psig, from about 100 psig to about 1400 psig, from about 100 psig to about 1200 psig, from about 100 psig to about 1000 psig, from about 100 psig to about 800 psig, from about 100 psig to about 600 psig, from about 100 psig to about 500 psig, from about 100 psig to about 400 psig, from about 100 psig to about 300 psig, from about 100 psig to about 200 psig, from about 200 psig to about 2000 psig, from about 200 psig to about 1800 psig, from about 200 psig to about 1600 psig, from about 200 psig to about 1400 psig, from about 200 psig to about 1200 psig, from about 200 psig to about 1000 psig, from about 200 psig to about 800 psig, from about 200 psig to about 600 psig, from about 200 psig to about 500 psig, from about 200 psig to about 400 psig, from about 200 psig to about 300 psig, from about 300 psig to about 2000 psig, from about 300 psig to about 1800 psig, from about 300 psig to about 1600 psig, from about 300 psig to about 1400 psig, from about 300 psig to about 1200 psig, from about 300 psig to about 1000 psig, from about 300 psig to about 800 psig, from about 300 psig to about 600 psig, from about 300 psig to about 500 psig, from about 300 psig to about 400 psig, from about 400 psig to about 2000 psig, from about 400 psig to about 1800 psig, from about 400 psig to about 1600 psig, from about 400 psig to about 1400 psig, from about 400 psig to about 1200 psig, from about 400 psig to about 1000 psig, from about 400 psig to about 800 psig, from about 400 psig to about 600 psig, from about 400 psig to about 500 psig, from about 500 psig to about 2000 psig, from about 500 psig to about 1800 psig, from about 500 psig to about 1600 psig, from about 500 psig to about 1400 psig, from about 500 psig to about 1200 psig, from about 500 psig to about 1000 psig, from about 500 psig to about 800 psig, from about 500 psig to about 600 psig, from about 600 psig to about 2000 psig, from about 600 psig to about 1800 psig, from about 600 psig to about 1600 psig, from about 600 psig to about 1400 psig, from about 600 psig to about 1200 psig, from about 600 psig to about 1000 psig, from about 600 psig to about 800 psig, from about 800 psig to about 2000 psig, from about 800 psig to about 1800 psig, from about 800 psig to about 1600 psig, from about 800 psig to about 1400 psig, from about 800 psig to about 1200 psig, from about 800 psig to about 1000 psig, from about 1000 psig to about 2000 psig, from about 1000 psig to about 1800 psig, from about 1000 psig to about 1600 psig, from about 1000 psig to about 1400 psig, from about 1000 psig to about 1200 psig, from about 1200 psig to about 2000 psig, from about 1200 psig to about 1800 psig, from about 1200 psig to about 1600 psig, from about 1200 psig to about 1400 psig, from about 1400 psig to about 2000 psig, from about 1400 psig to about 1800 psig, from about 1400 psig to about 1600 psig, from about 1600 psig to about 2000 psig, from about 1600 psig to about 1800 psig, or from about 1800 psig to about 2000 psig. In particular, a pressure in the reaction zone can be from about 15 psig to about 1500 psig.

C. Catalyst

The at least one reactor (e.g., moving bed reactor) comprises a catalyst for promoting conversion of the feedstock (e.g., oxygenates and/or olefin) to a hydrocarbon product (e.g., $C_2$-$C_{22}$ hydrocarbon product, etc.). In some embodiments, he catalyst may comprise particles having a substantially spherical shape.

Typically, the catalyst comprises at least one molecular sieve material, which may have a framework type selected from the following group of framework types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, TI-HW, ISV, ITE, ITH, ITW, TWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, ET, VFI, VNI, VSV, WEI, WEN, YUG, ZNI, and ZON. Particular examples of these framework types can include AEL, AFO, AHT, ATO, CAN, EUO, FER, HEU, IMF, ITH, LAU, MEL, MFI, MFS, MRE, MSE, MTT, MTW, MWW, NES, OBW, OSI, PON, RRO, SFF, SFG, STF, STI, SZR, TON, TUN and VET.

A suitable molecular sieve material may be a zeolite with the above-mentioned framework type. Generally, the zeolite employed in the present catalyst composition can typically have a silica to alumina molar ratio of at least 20, e.g., from about 20 to about 200. Suitable zeolites can include, but are not necessarily limited to, ZSM-5, ZSM-12, ZSM-23, ZSM-48, ZSM-57, MCM-22 and the like, as well as intergrowths and combinations thereof. In certain embodiments, the zeolite can comprise, consist essentially of, or be ZSM-5.

Additionally or alternatively, the zeolite may be present at least partly in hydrogen form in the catalyst (e.g., HZSM-5). Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

Additionally or alternatively, the molecular sieve material may be an aluminophosphate (i.e., ALPO). Suitable ALPOs can include, but are not necessarily limited to AlPO-11, AlPO-H2, AlPO-31 and AlPO-41.

Additionally or alternatively, the molecular sieve material may be a silicoaluminophosphate (i.e., SAPO). Suitable SAPOs can include, but are not necessarily limited to SAPO-11, SAPO-41, and/or SAPO-31.

Further additional suitable molecular sieves may include, but are not necessarily limited to GeAPO-11, MnAPO-11, MnAPO-41, MnAPSO-41, MAPO-31 (M=Mn, Ni, Zn, Mg, Co, Cr, Cu, Cd), VAPO-31, cancrinite (e.g., basic, hydrate, synthetics), [Al—Ge—O]-CAN, [Co—P—O]-CAN, [Ga—Ge—O]-CAN, [Ga—Si—O]-CAN, [Zn—P—O]-CAN, [Li—Cs][Al—Si—O]-CAN, [Li—Tl][Al—Si—O]-CAN, davyne, ECR-5, microsommite, tiptopite, vishnevite, EU-1, [B—Si—O]-EUO, TPZ-3, o-FDBDM-ZSM-50, ferrierite, [B—Si—O]-FER, [Ga—Si—O]-FER, [Si—O]-FER, FU-9, SIS-6, monoclinic ferrierite, NU-23, Sr-D, heulandite, clinoptilolite, dehyd. Ca,NH$_4$-heulandite, heulandite-Ba, LZ-219, IM-5, ITQ-13, Al-ITQ-13, IM-7, laumontite, [Co—Ga—P—O]-LAU, [Fe—Ga—P—O]-LAU, [Mn—Ga—P—O]-LAU, [Zn—Al—As—O]-LAU, [Zn—Ga—P—O]-LAU, leonhardite, Na,K-rich laumontite, primary leonhardite, synthetic laumontite, [DEOTA][Si—B—O]-MEL, Bor-D, boralite-D, SSZ-46, Silicate 2, TS-2, [As—Si—O]-MFI, [Fe—Si—O]-MFI, [Ga—Si—O]-MFI, AMS-1B, AZ-1, Bor-C, boralite, encilite, FZ-1, FeS-1, LZ-105, MnS-1, monoclinic H-ZSM-5, mutinaite, NU-4, NU-5, Silicalite, TS-1, TSZ, TSZ-II, TZ-01, USC-4, USI-108, ZBH, ZKQ-IB, ZMQ-TB, organic-free ZSM-5, COK-5, [B—Si—O]-MTW, [Ga—Si—O]-MTW, CZH-5, NU-13, TPZ-12, Theta-3, VS-12, [Ga—Si—O]-MWW, [Ti—Si—O]-MTW, ERB-1, ITQ-1, PSH-3, MCM-68, EU-13, ISI-4, KZ-1, NU-87, gottardiite, OSB-2, UiO-6, IST-1, RUB-41, SSZ-44, STF-SFF intermediates, SSZ-58, SSZ-35, ITQ-9, Mu-26, stilbite (non-synthetic and synthetic), barrerite (non-synthetic and synthetic), stellerite (non-synthetic and synthetic), TNU-10, SUZ-4, Theta-1, ISI-1, KZ-2, NU-10, TNU-9, Mu-18, UZM-5, IM-10, IM-6, IM-12, ITQ-15 and VPI-8. A person of ordinary skill in the art knows how to make the aforementioned frameworks and molecular sieves. For example, see the references provided in the International Zeolite Association's database of zeolite structures found at www.iza-structure.org/databases.

The catalysts described herein can include and/or be enhanced by a transition metal. Catalyst compositions herein can include a Group 10-12 element or combinations thereof, of the Periodic Table. Exemplary Group 10 elements include, e.g., nickel, palladium, and/or platinum, particularly nickel. Exemplary Group 11 elements include, e.g., copper, silver, and/or gold, particularly copper. Exemplary Group 12 elements include e.g., zinc and/or cadmium. Preferably the transition metal is a Group 12 metal from the UPAC periodic table (sometimes designated as Group IIB) such as Zn and/or Cd. In particular embodiments, nickel, copper and/or zinc, particularly zinc, may be used. The Group 10-12 element can be incorporated into the catalyst by any convenient method, such as by impregnation or by ion exchange. After impregnation or ion exchange, the Group 10-12 element-enhanced catalyst can be treated in an oxidizing environment (air) or an inert atmosphere at a temperature of about 400° C. to about 700° C.

The amount of Group 10-12 element can be related to the molar amount of aluminum present in the catalyst (e.g., zeolite). In some advantageous embodiments, the molar ratio of the Group 10-12 element to aluminum in the catalyst can be about 0.1 to about 1.3, e.g., from about 0.1 to about 1.2, from about 0.1 to about 1.0, from about 0.1 to about 0.8, from about 0.1 to about 0.4, from about 0.1 to about 0.3, from about 0.1 to about 0.2, from about 0.2 to about 1.3, from about 0.2 to about 1.2, from about 0.2 to about 1.0, from about 0.2 to about 0.8, from about 0.2 to about 0.4, from about 0.2 to about 0.3, from about 0.3 to about 1.3, from about 0.3 to about 1.2, from about 0.3 to about 1.0, from about 0.3 to about 0.8, from about 0.3 to about 0.4, from about 0.4 to about 1.3, from about 0.4 to about 1.2, from about 0.4 to about 1.0, from about 0.4 to about 0.8, from about 0.8 to about 1.3, from about 0.8 to about 1.2, from about 0.8 to about 1.0, from about 1.0 to about 1.3, from about 1.0 to about 1.2, or from about 1.2 to about 1.3. Still further additionally or alternately, the amount of Group 10-12 element can be expressed as a weight percentage of the catalyst, such as from about 0.1 wt % to about 20 wt %, from about 0.1 wt % to about 10 wt %, from about 0.1 wt % to about 5.0 wt %, from about 0.1 wt % to about 2.0 wt %, from about 0.1 wt % to about 1.5 wt %, from about 0.1 wt % to about 1.2 wt %, from about 0.1 wt % to about 1.0 wt %, from about 0.1 wt % to about 0.75 wt %, from about 0.1 wt % to about 0.5 wt %, from about 0.1 wt % to about 0.25 wt %, from about 0.25 wt % to about 20 wt %, from about 0.25 wt % to about 10 wt %, from about 0.25 wt % to about 5.0 wt %, from about 0.25 wt % to about 2.0 wt %, from about 0.25 wt % to about 1.5 wt %, from about 0.25 wt % to about 1.2 wt %, from about 0.25 wt % to about 1.0 wt %, from about 0.25 wt % to about 0.75 wt %, from about 0.25 wt % to about 0.5 wt %, from about 0.5 wt % to about 20 wt %, from about 0.5 wt % to about 10 wt %, from about 0.5 wt % to about 5.0 wt %, from about 0.5 wt % to about 2.0 wt %, from about 0.5 wt % to about 1.5 wt %, from about 0.5 wt % to about 1.2 wt %, from about 0.5 wt % to about 1.0 wt %, from about 0.5 wt % to about 0.75 wt %, from about 0.75 wt % to about 20 wt %, from about 0.75 wt % to about 10 wt %, from about 0.75 wt % to about 5.0 wt %, from about 0.75 wt % to about 2.0 wt %, from about 0.75 wt % to about 1.5 wt %, from about 0.75 wt % to about 1.2 wt %, from about 0.75 wt % to about 1.0 wt %, from about 1.0 wt % to about 20 wt %, from about 1.0 wt % to about 10 wt %, from about 1.0 wt % to about 5.0 wt %, from about 1.0 wt % to about 2.0 wt %, from about 1.0 wt % to about 1.5 wt %, from about 1.0 wt % to about 1.2 wt %, from about 1.2 wt % to about 20 wt %, from about 1.2 wt % to about 10 wt %, from about 1.2 wt % to about 5.0 wt %, from about 1.2 wt % to about 2.0 wt %, from about 1.2 wt % to about 1.5 wt %, from about 1.5 wt % to about 20 wt %, from about 1.5 wt % to about 10 wt %, from about 1.5 wt % to about 5.0 wt %, from about 1.5 wt % to about 2.0 wt %, from about 2.0 wt % to about 20 wt %, from about 2.0 wt % to about 10 wt %, from about 2.0 wt % to about 5.0 wt %, from about 5.0 wt % to about 20 wt %, from about 5.0 wt % to about 10 wt %, or from about 10 wt % to about 20 wt % of the Group 10-12 element, based on the total weight of the catalyst composition excluding the weight of any binder, if present.

Additionally or alternatively, the catalyst described herein may also include at least one Group 2 and/or a Group 3 element. As used herein the term "Group 3" is intended to include elements in the Lanthanide series of the Periodic Table. In any embodiment, one or more Group 2 elements (e.g., Be, Mg, Ca, Sr, Ba and Ra) may be used. In other embodiments, one or Group 3 element (e.g., Sc and Y), a Lanthanide (e.g., La, Ce, Pr, Nd, Sm, Eu, Gd, Tb, Dy, Ho, Er, Tm, Yb and Lu). Actinides (e.g., Ac, Th, Pa, U, Np, Pu, Am, Cm, Bk, Cf, Es, Fm, Md, No, Lr) may be used as well. When present, the total weight of the at least one Group 2 and/or Group 3 elements is from about 0.1 to about 20.0 wt %, based on the total weight of the catalyst composition excluding the weight of any binder if present. In any embodiment, the amount of the at least one Group 2 and/or a Group 3 element may be about 0.25 to about 10 wt %, e.g., about 0.5 to about 5.0 wt %, about 0.75 to about 2.0 wt %, or about 1.0 to about 1.5 wt %. The presence of Group 2 and/or Group 3 element is believed to reduce coke formation.

The catalysts described herein can be pretreated with steam prior to use in the reactor.

Additionally or alternatively, the present catalyst can contain phosphorus in an amount between about 0.01 wt % and about 3 wt % elemental phosphorus, e.g., between about 0.05 wt % and about 2 wt %, of the total catalyst composition. The phosphorus can be added to the catalyst composition at any stage during synthesis of the catalyst and/or formulation of the catalyst and binder into the catalyst composition. Generally, phosphorus addition can be achieved by spraying and/or impregnating the final catalyst composition (and/or a precursor thereto) with a solution of a phosphorus compound. Suitable phosphorus compounds can include, but are not limited to, phosphinic [$H_2PO(OH)$], phosphonic [$HPO(OH)_2$], phosphinous, phosphorus, and phosphoric [$PO(OH)_3$] acids, salts and esters of such acids, phosphorus halides, and the like, and combinations thereof. After phosphorus treatment, the catalyst can generally be calcined, e.g., in air at a temperature from about 400° C. to about 700° C. to convert the phosphorus to an oxide form.

In one embodiment, the catalyst can be modified with up to 3 wt % phosphorous for improved stability.

Catalyst Binder

The catalysts described herein can optionally be employed in combination with a support or binder material (binder). The binder is preferably an inert, non-alumina containing material, such as a porous inorganic oxide support or a clay binder. One such preferred inorganic oxide is silica. Other examples of such binder material include, but are not limited to zirconia, magnesia, titania, thoria and boria. These materials can be utilized in the form of a dried inorganic oxide gel or as a gelatinous precipitate. Suitable examples of clay binder materials include, but are not limited to, bentonite and kieselguhr. The relative proportion of catalyst to binder material to be utilized can be from about 30 wt % to about 98 wt %, advantageously from about 50 wt % to about 80 wt %. The bound catalyst can be in the form of an extrudate, beads or fluidizable microspheres.

D. Separation of the Mixture

The process may further comprise passing the mixture (e.g., three-phase mixture of converted hydrocarbon product and unconverted feedstock) to a stripping zone in the at least one reactor (e.g., moving bed reactor); and separating the mixture (e.g., three-phase) in the stripping zone.

The separating may comprise collecting the mixture (e.g., three-phase) in at least one stripping chamber 4 as described above, e.g., having a top inlet 5 and a bottom outlet 6, defining perforations 7 therein as described above and the top inlet 5 having a diameter greater than a diameter of the bottom outlet 6. In particular, the at least one stripping chamber 4 is generally disposed between at least one inlet chamber 2 as described above and at least one collection chamber 8 as described above. The at least one stripping chamber 4 may generally have a (frusto)conical shape. Additionally, the at least one stripping chamber 4 may further comprise a stripping interface section 11 having a first angle (e.g., ~5° to ~30°, ~5° to ~10°, or ~7° to ~8°) and/or a guide section 12 having a second angle (e.g., ~7° to ~45°, ~25° to ~35°, or ~30° to ~35°), particularly where the first angle can be less than or equal to the second angle.

Additionally or alternatively, the separating may further comprise introducing a stripping fluid as described above into the at least one inlet chamber 2, wherein the stripping fluid flows into the at least one stripping chamber 4 through the perforations 7 whereby at least a portion of the converted hydrocarbon product and optionally, the unconverted feedstock are stripped from the spent catalyst. Particularly, the stripping fluid generally flows in a direction cross-current to a flow of the spent catalyst. Additionally or alternatively, the stripping fluid may enter the at least one inlet chamber 2 at a flow rate, e.g. from about 1 to about 40 times, a flow rate of the feedstock into the at least one reactor (e.g., moving bed reactor).

Additionally or alternatively, the separating may further comprise passing the converted hydrocarbon product and optionally, the unconverted feedstock stripped from the spent catalyst through the perforations 7 into the at least one collection chamber 8; and passing the stripped catalyst through the bottom outlet 6 of the at least one stripping chamber 4. Additionally or alternatively, the stripping fluid may pass through the perforations 7 into the at least one collection chamber 8. Additionally or alternatively, once passed into the at least one collection chamber 8, the stripping fluid, the converted hydrocarbon product and/or the unconverted feedstock may further exit the at least one collection chamber 8 via the at least one outlet 9.

E. Hydrocarbon Product

The converted hydrocarbon product may be in a single phase (e.g., gas or liquid) or may be in a mixed phase (e.g., gas and liquid). Additionally, the converted hydrocarbon product produced may comprise a variety of hydrocarbon compositions produced from the reaction of the feedstock in the reactor. The hydrocarbon compositions typically have mixtures of hydrocarbon compounds having from 2 to 30 carbon atoms ($C_2$-$C_{30}$ hydrocarbons), from 2 to 25 carbon atoms ($C_2$-$C_{25}$ hydrocarbons), from 2 to 20 carbon atoms ($C_2$-$C_{20}$ hydrocarbons), from 2 to 15 carbon atoms ($C_2$-$C_{15}$ hydrocarbons), from 2 to 10 carbon atoms ($C_2$-$C_{10}$ hydrocarbons), from 2 to 8 carbon atoms ($C_2$-$C_8$ hydrocarbons), from 2 to 6 carbon atoms ($C_2$-$C_6$ hydrocarbons), from 2 to 4 carbon atoms ($C_2$-$C_4$ hydrocarbons), from 5 to 12 carbon atoms ($C_5$-$C_{12}$ hydrocarbons), and from 5 to 9 carbon atoms ($C_5$-$C_9$ hydrocarbons). Particularly, the hydrocarbon product comprises $C_2$-$C_{25}$ hydrocarbons. The $C_2$-$C_{25}$ hydrocarbons may be present in the hydrocarbon product in amount from about 20 wt % to about 100 wt %, e.g., from about 20 wt % to about 95 wt %, from about 20 wt % to about 90 wt %, from about 20 wt % to about 85 wt %, from about 20 wt % to about 80 wt %, from about 20 wt % to about 75 wt %, from about 20 wt % to about 70 wt %, from about 20 wt % to about 65 wt %, from about 20 wt % to about 60 wt %, from about 20 wt % to about 55 wt %, from about 20 wt % to about 50 wt %, from about 20 wt % to about 45 wt %, from about 20 wt % to about 40 wt %, from about 20 wt % to about 35 wt %, from about 20 wt % to about 30 wt %, from about 20 wt % to about 25 wt %, from about 25 wt % to about 100 wt %, from about 25 wt % to about 95 wt %, from about 25 wt % to about 90 wt %, from about 25 wt % to about 85 wt %, from about 25 wt % to about 80 wt %, from about 25 wt % to about 75 wt %, from about 25 wt % to about 70 wt %, from about 25 wt % to about 65 wt %, from about 25 wt % to about 60 wt %, from about 25 wt % to about 55 wt %, from about 25 wt % to about 50 wt %, from about 25 wt % to about 45 wt %, from about 25 wt % to about 40 wt %, from about 25 wt % to about 35 wt %, from about 25 wt % to about 30 wt %, from about 30 wt % to about 100 wt %, from about 30 wt % to about 95 wt %, from about 30 wt % to about 90 wt %, from about 30 wt % to about 85 wt %, from about 30 wt % to about 80 wt %, from about 30 wt % to about 75 wt %, from about 30 wt % to about 70 wt %, from about 30 wt % to about 65 wt %, from about 30 wt % to about 60 wt %, from about 30 wt % to about 55 wt %, from about 30 wt % to about 50 wt %, from about 30 wt % to about 45 wt %, from about 30 wt % to about 40 wt %, from about 30 wt % to about 35 wt %, from about 35 wt % to about 100 wt %, from about 35 wt % to about 95 wt %, from about 35 wt % to about 90 wt %, from about 35 wt % to about 85 wt %, from about 35 wt % to about 80 wt %, from about 35 wt % to about 75 wt %, from about 35 wt % to about 70 wt %, from about 35 wt % to about 65 wt %, from about 35 wt % to about 60 wt %, from about 35 wt % to about 55 wt %, from about 35 wt % to about 50 wt %, from about 35 wt % to about 45 wt %, from about 35 wt % to about 40 wt %, from about 40 wt % to about 100 wt %, from about 40 wt % to about 95 wt %, from about 40 wt % to about 90 wt %, from about 40 wt % to about 85 wt %, from about 40 wt % to about 80 wt %, from about 40 wt % to about 75 wt %, from about 40 wt % to about 70 wt %, from about 40 wt % to about 65 wt %, from about 40 wt % to about 60 wt %, from about 40 wt % to about 55 wt %, from about 40 wt % to about 50 wt %, from about 40 wt % to about 45 wt %, from about 45 wt % to about 100 wt %, from about 45 wt % to about 95 wt %, from about 45 wt % to about 90 wt %, from about 45 wt % to about 85 wt %, from about 45 wt % to about 80 wt %, from about 45 wt % to about 75 wt %, from about 45 wt % to about 70 wt %, from about 45 wt % to about 65 wt %, from about 45 wt % to about 60 wt %, from about 45 wt % to about 55 wt %, from about 45 wt % to about 50 wt %, from about 50 wt % to about 100 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 65 wt %, from about 50 wt % to about 60 wt %, from about 50 wt % to about 55 wt %, from about 55 wt % to about 100 wt %, from about 55 wt % to about 95 wt %, from about 55 wt % to about 90 wt %, from about 55 wt % to about 85 wt %, from about 55 wt % to about 80 wt %, from about 55 wt % to about 75 wt %, from about 55 wt % to about 70 wt %, from about 55 wt % to about 65 wt %, from about 55 wt % to about 60 wt %, from about 60 wt % to about 100 wt %, from about 60 wt % to about 95 wt %, from about 60 wt % to about 90 wt %, from about 60 wt % to about 85 wt %, from about 60 wt % to about 80 wt %, from about 60 wt % to about 75 wt %, from about 60 wt % to about 70 wt %, from about 60 wt % to about 65 wt %, from about 65 wt % to about 100 wt %, from about 65 wt % to about 95 wt %, from about 65 wt % to about 90 wt %, from about 65 wt % to about 85 wt %, from about 65 wt % to about 80 wt %, from about 65 wt % to about 75 wt %, from about 65 wt % to about 70 wt %, from about 70 wt % to about 100 wt %, from about 70 wt % to about 95 wt %, from about 70 wt % to about 90 wt %, from about 70 wt % to about 85 wt %, from about 70 wt % to about 80 wt %, from about 70 wt % to about 75 wt %, from about 75 wt % to about 100 wt %, from about 75 wt % to about 95 wt %, from about 75 wt % to about 90 wt %, from about 75 wt % to about 85 wt %, from about 75 wt % to about 80 wt %, from about 80 wt % to about 100 wt %, from about 80 wt % to about 95 wt %, from about 80 wt % to about 90 wt %, from about 80 wt % to about 85 wt %, from about 85 wt % to about 100 wt %, from about 85 wt % to about 95 wt %, from about 85 wt % to about 90 wt %, from about 90 wt % to about 100 wt %, from about 90 wt % to about 95 wt %, or from about 95 wt % to about 100 wt %.

Additionally or alternatively, the hydrocarbon product may comprise one or more olefins, e.g., having 2 to 20 carbons atoms, particularly 2 to 8 carbon atoms or 2 to 5 carbon atoms. The one or more olefins may be present in the hydrocarbon product in amount from about 1.0 wt % to about 100 wt %, e.g., from about 1.0 wt % to about 95 wt %, from about 1.0 wt % to about 90 wt %, from about 1.0 wt % to about 85 wt %, from about 1.0 wt % to about 80 wt %, from about 1.0 wt % to about 75 wt %, from about 1.0 wt % to about 70 wt %, from about 1.0 wt % to about 60 wt %, from about 1.0 wt % to about 50 wt %, from about 1.0 wt % to about 40 wt %, from about 1.0 wt % to about 30 wt %, from about 1.0 wt % to about 25 wt %, from about 1.0 wt % to about 20 wt %, from about 1.0 wt % to about 10 wt %, from about 1.0 wt % to about 5.0 wt %, from about 1.0 wt % to about 2.0 wt %, from about 2.0 wt % to about 100 wt %, from about 2.0 wt % to about 95 wt %, from about 2.0 wt % to about 90 wt %, from about 2.0 wt % to about 85 wt %, from about 2.0 wt % to about 80 wt %, from about 2.0 wt % to about 75 wt %, from about 2.0 wt % to about 70 wt %, from about 2.0 wt % to about 60 wt %, from about 2.0 wt % to about 50 wt %, from about 2.0 wt % to about 40 wt %, from about 2.0 wt % to about 30 wt %, from about 2.0 wt % to about 25 wt %, from about 2.0 wt % to about 20 wt %, from about 2.0 wt % to about 10 wt %, from about 2.0 wt % to about 5.0 wt %, from about 5.0 wt % to about 100 wt %, from about 5.0 wt % to about 95 wt %, from about 5.0 wt % to about 90 wt %, from about 5.0 wt % to about 85 wt %, from about 5.0 wt % to about 80 wt %, from about 5.0 wt % to about 75 wt %, from about 5.0 wt % to about 70 wt %, from about 5.0 wt % to about 60 wt %, from about 5.0 wt % to about 50 wt %, from about 5.0 wt % to about 40 wt %, from about 5.0 wt % to about 30 wt %, from about 5.0 wt % to about 25 wt %, from about 5.0 wt % to about 20 wt %, from about 5.0 wt % to about 10 wt %, from about 10 wt % to about 100 wt %, from about 10 wt % to about 95 wt %, from about 10 wt % to about 90 wt %, from about 10 wt % to about 85 wt %, from about 10 wt % to about 80 wt %, from about 10 wt % to about 75 wt %, from about 10 wt % to about 70 wt %, from about 10 wt % to about 60 wt %, from about 10 wt % to about 50 wt %, from about 10 wt % to about 40 wt %, from about 10 wt % to about 30 wt %, from about 10 wt % to about 25 wt %, from about 10 wt % to about 20 wt %, from about 20 wt % to about 100 wt %, from about 20 wt % to about 95 wt %, from about 20 wt % to about 90 wt %, from about 20 wt % to about 85 wt %, from about 20 wt % to about 80 wt %, from about 20 wt % to about 75 wt %, from about 20 wt % to about 70 wt %, from about 20 wt % to about 60 wt %, from about 20 wt % to about 50 wt %, from about 20 wt % to about 40 wt %, from about 20 wt % to about 30 wt %, from about 20 wt % to about 25 wt %, from about 25 wt % to about 100 wt %, from about 25 wt % to about 95 wt %, from about 25 wt % to about 90 wt %, from about 25 wt % to about 85 wt %, from about 25 wt % to about 80 wt %, from about 25 wt % to about 75 wt %, from about 25 wt % to about 70 wt %, from about 25 wt % to about 60 wt %, from about 25 wt % to about 50 wt %, from about 25 wt % to about 40 wt %, from about 25 wt % to about 30 wt %, from about 30 wt % to about 100 wt %, from about 30 wt % to about 95 wt %, from about 30 wt % to about 90 wt %, from about 30 wt % to about 85 wt %, from about 30 wt % to about 80 wt %, from about 30 wt % to about 75 wt %, from about 30 wt % to about 70 wt %, from about 30 wt % to about 60 wt %, from about 30 wt % to about 50 wt %, from about 30 wt % to about 40 wt %, from about 40 wt % to about 100 wt %, from about 40 wt % to about 95 wt %, from about 40 wt % to about 90 wt %, from about 40 wt % to about 85 wt %, from about 40 wt % to about 80 wt %, from about 40 wt % to about 75 wt %, from about 40 wt % to about 70 wt %, from about 40 wt % to about 60 wt %, from about 40 wt % to about 50 wt %, from about 50 wt % to about 100 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 60 wt %, from about 60 wt % to about 100 wt %, from about 60 wt % to about 95 wt %, from about 60 wt % to about 90 wt %, from about 60 wt % to about 85 wt %, from about 60 wt % to about 80 wt %, from about 60 wt % to about 75 wt %, from about 60 wt % to about 70 wt %, from about 70 wt % to about 100 wt %, from about 70 wt % to about 95 wt %, from about 70 wt % to about 90 wt %, from about 70 wt % to about 85 wt %, from about 70 wt % to about 80 wt %, from about 70 wt % to about 75 wt %, from about 75 wt % to about 100 wt %, from about 75 wt % to about 95 wt %, from about 75 wt % to about 90 wt %, from about 75 wt % to about 85 wt %, from about 75 wt % to about 80 wt %, from about 80 wt % to about 100 wt %, from about 80 wt % to about 95 wt %, from about 80 wt % to about 90 wt %, from about 80 wt % to about 85 wt %, from about 85 wt % to about 100 wt %, from about 85 wt % to about 95 wt %, from about 85 wt % to about 90 wt %, from about 90 wt % to about 100 wt %, from about 90 wt % to about 95 wt %, or from about 95 wt % to about 100 wt %.

Additionally or alternatively, the hydrocarbon product may comprise one or more paraffins, e.g. having 1 to 20 carbon atoms, particularly 1 to 12 carbons atoms and particularly, 1 to 8 carbon atoms. The one or more paraffins may be present in the hydrocarbon product in an amount from about 1.0 wt % to about 70 wt %, e.g., from about 1.0 wt % to about 60 wt %, from about 1.0 wt % to about 50 wt %, from about 1.0 wt % to about 40 wt %, from about 1.0 wt % to about 30 wt %, from about 1.0 wt % to about 25 wt %, from about 1.0 wt % to about 20 wt %, from about 1.0 wt % to about 10 wt %, from about 1.0 wt % to about 5.0 wt %, from about 1.0 wt % to about 2.0 wt %, from about 2.0 wt % to about 70 wt %, from about 2.0 wt % to about 60 wt %, from about 2.0 wt % to about 50 wt %, from about 2.0 wt % to about 40 wt %, from about 2.0 wt % to about 30 wt %, from about 2.0 wt % to about 25 wt %, from about 2.0 wt % to about 20 wt %, from about 2.0 wt % to about 10 wt %, from about 2.0 wt % to about 5.0 wt %, from about 5.0 wt % to about 70 wt %, from about 5.0 wt % to about 60 wt %, from about 5.0 wt % to about 50 wt %, from about 5.0 wt % to about 40 wt %, from about 5.0 wt % to about 30 wt %, from about 5.0 wt % to about 25 wt %, from about 5.0 wt % to about 20 wt %, from about 5.0 wt % to about 10 wt %, from about 10 wt % to about 70 wt %, from about 10 wt % to about 60 wt %, from about 10 wt % to about 50 wt %, from about 10 wt % to about 40 wt %, from about 10 wt % to about 30 wt %, from about 10 wt % to about 25 wt %, from about 10 wt % to about 20 wt %, from about 20 wt % to about 70 wt %, from about 20 wt % to about 60 wt %, from about 20 wt % to about 50 wt %, from about 20 wt % to about 40 wt %, from about 20 wt % to about 30 wt %, from about 20 wt % to about 25 wt %, from about 25 wt % to about 70 wt %, from about 25 wt % to about 60 wt %, from about 25 wt % to about 50 wt %, from about 25 wt % to about 40 wt %, from about 25 wt % to about 30 wt %, from about 30 wt % to about 70 wt %, from about 30 wt % to about 60 wt %, from about 30 wt % to about 50 wt %, from about 30 wt % to about 40 wt %, from about 40 wt % to about 70 wt %, from about 40 wt % to about 60 wt %, from about 40 wt % to about 50 wt %, from about 50 wt % to about 70 wt %, from about 50 wt % to about 60 wt %, or from about 60 wt % to about 70 wt %.

Additionally or alternatively, the hydrocarbon product may comprise one or more aromatics, e.g., having 6 to 18 carbon atoms, particularly 6 to 12 carbon atoms. The one or more aromatics may be present in the hydrocarbon product in an amount from about 1.0 wt % to about 65 wt %, e.g., from about 1.0 wt % to about 60 wt %, from about 1.0 wt % to about 50 wt %, from about 1.0 wt % to about 40 wt %, from about 1.0 wt % to about 30 wt %, from about 1.0 wt % to about 25 wt %, from about 1.0 wt % to about 20 wt %, from about 1.0 wt % to about 10 wt %, from about 1.0 wt % to about 5.0 wt %, from about 1.0 wt % to about 2.0 wt %, from about 2.0 wt % to about 65 wt %, from about 2.0 wt % to about 60 wt %, from about 2.0 wt % to about 50 wt %, from about 2.0 wt % to about 40 wt %, from about 2.0 wt % to about 30 wt %, from about 2.0 wt % to about 25 wt %, from about 2.0 wt % to about 20 wt %, from about 2.0 wt % to about 10 wt %, from about 2.0 wt % to about 5.0 wt %, from about 5.0 wt % to about 65 wt %, from about 5.0 wt % to about 60 wt %, from about 5.0 wt % to about 50 wt %, from about 5.0 wt % to about 40 wt %, from about 5.0 wt % to about 30 wt %, from about 5.0 wt % to about 25 wt %, from about 5.0 wt % to about 20 wt %, from about 5.0 wt % to about 10 wt %, from about 10 wt % to about 65 wt %, from about 10 wt % to about 60 wt %, from about 10 wt % to about 50 wt %, from about 10 wt % to about 40 wt %, from about 10 wt % to about 30 wt %, from about 10 wt % to about 25 wt %, from about 10 wt % to about 20 wt %, from about 20 wt % to about 65 wt %, from about 20 wt % to about 60 wt %, from about 20 wt % to about 50 wt %, from about 20 wt % to about 40 wt %, from about 20 wt % to about 30 wt %, from about 20 wt % to about 25 wt %, from about 25 wt % to about 65 wt %, from about 25 wt % to about 60 wt %, from about 25 wt % to about 50 wt %, from about 25 wt % to about 40 wt %, from about 25 wt % to about 30 wt %, from about 30 wt % to about 65 wt %, from about 30 wt % to about 60 wt %, from about 30 wt % to about 50 wt %, from about 30 wt % to about 40 wt %, from about 40 wt % to about 65 wt %, from about 40 wt % to about 60 wt %, from about 40 wt % to about 50 wt %, from about 50 wt % to about 65 wt %, from about 50 wt % to about 60 wt %, or from about 60 wt % to about 65 wt %.

Additionally or alternatively, the hydrocarbon product may comprise one or more aldehydes, alcohols and/or ketones, e.g. having 1 to 30 carbon atoms, particularly 1 to 20 carbons atoms or 1 to 10 carbon atoms. The one or more aldehydes, alcohols and/or ketones may be present in the hydrocarbon product in an amount from about 1.0 wt % to about 70 wt %, e.g., from about 1.0 wt % to about 60 wt %, from about 1.0 wt % to about 50 wt %, from about 1.0 wt % to about 40 wt %, from about 1.0 wt % to about 30 wt %, from about 1.0 wt % to about 25 wt %, from about 1.0 wt % to about 20 wt %, from about 1.0 wt % to about 10 wt %, from about 1.0 wt % to about 5.0 wt %, from about 1.0 wt % to about 2.0 wt %, from about 2.0 wt % to about 70 wt %, from about 2.0 wt % to about 60 wt %, from about 2.0 wt % to about 50 wt %, from about 2.0 wt % to about 40 wt %, from about 2.0 wt % to about 30 wt %, from about 2.0 wt % to about 25 wt %, from about 2.0 wt % to about 20 wt %, from about 2.0 wt % to about 10 wt %, from about 2.0 wt % to about 5.0 wt %, from about 5.0 wt % to about 70 wt %, from about 5.0 wt % to about 60 wt %, from about 5.0 wt % to about 50 wt %, from about 5.0 wt % to about 40 wt %, from about 5.0 wt % to about 30 wt %, from about 5.0 wt % to about 25 wt %, from about 5.0 wt % to about 20 wt %, from about 5.0 wt % to about 10 wt %, from about 10 wt % to about 70 wt %, from about 10 wt % to about 60 wt %, from about 10 wt % to about 50 wt %, from about 10 wt % to about 40 wt %, from about 10 wt % to about 30 wt %, from about 10 wt % to about 25 wt %, from about 10 wt % to about 20 wt %, from about 20 wt % to about 70 wt %, from about 20 wt % to about 60 wt %, from about 20 wt % to about 50 wt %, from about 20 wt % to about 40 wt %, from about 20 wt % to about 30 wt %, from about 20 wt % to about 25 wt %, from about 25 wt % to about 70 wt %, from about 25 wt % to about 60 wt %, from about 25 wt % to about 50 wt %, from about 25 wt % to about 40 wt %, from about 25 wt % to about 30 wt %, from about 30 wt % to about 70 wt %, from about 30 wt % to about 60 wt %, from about 30 wt % to about 50 wt %, from about 30 wt % to about 40 wt %, from about 40 wt % to about 70 wt %, from about 40 wt % to about 60 wt %, from about 40 wt % to about 50 wt %, from about 50 wt % to about 70 wt %, from about 50 wt % to about 60 wt %, or from about 60 wt % to about 70 wt %.

F. Separation of Hydrocarbons

The process may further comprise separating various hydrocarbons in the hydrocarbon product, e.g., separating the $C_2$-$C_{22}$ hydrocarbons from the hydrocarbon product. Separation may be accomplished by any suitable separation means and combination thereof, e.g., distillation tower, simulated moving-bed separation unit, high pressure separator, low pressure separator, high temperature separator, low temperature separator, flash drum, etc. For example, $C_{2-}$ light gas can be separated from $C_{3+}$ product in, for example, a fractionating column (e.g., de-ethanizer) Additionally or alternatively, the $C_{3+}$ product can be sent to a stabilizer (e.g., de-propanizer) where the $C_3$ and part of the $C_{4+}$ hydrocarbon components can be removed from the hydrocarbon product.

G. Further Processing

Additionally or alternatively, the de-ethanizer bottom product can be fed into a gasoline splitter where it can be separated into light and heavy gasoline fractions. The heavy gasoline fraction, which may contain durene, can be passed to a heavy gasoline treatment (HGT) reactor for reduction of durene content. In the HGT process, the heavy gasoline, comprising primarily aromatics, can be processed over a multifunctional metal acid catalyst. The following reactions can occur: disproportionation, isomerization, transalkylation, ring saturation, and dealkylation/cracking wherein durene content can be further reduced.

Additionally or alternatively, the $C_3$ and part of the $C_4$ hydrocarbon components (e.g., propylenes, and butenes) can be fed to an alkylation unit for conversion to $C_{5+}$ product.

Further additionally or alternatively, olefinic distillate products may be further hydrotreated to final paraffinic distillate products.

IV. Reaction System

Figure 4:
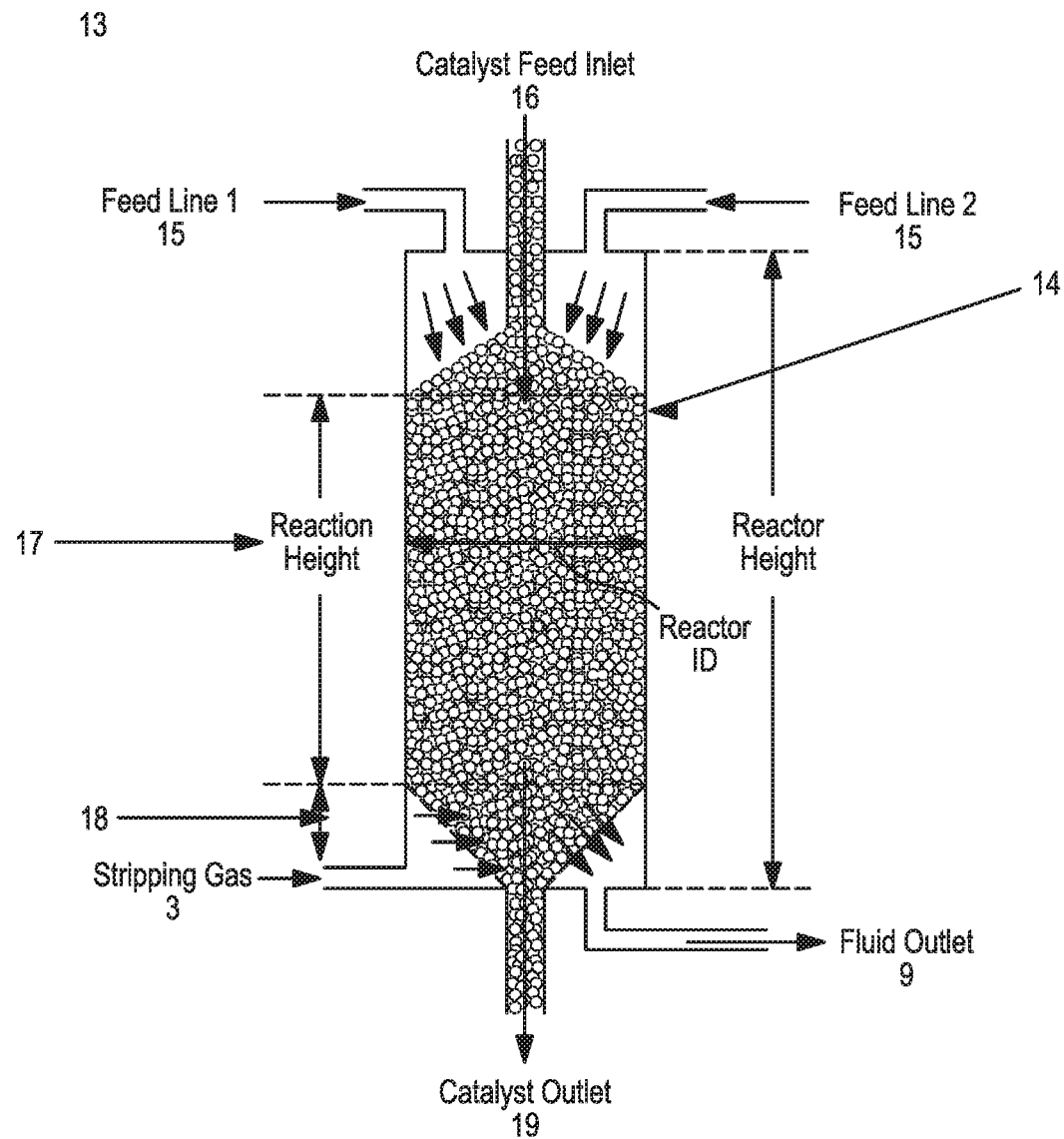
FIG. 4 illustrates an embodiment of a reaction system 13.

In another embodiment, a reaction system for converting a feedstock as described above to a hydrocarbon product as described above is provided. As shown in FIG. 4, the reaction system may comprise at least one moving bed reactor unit 13 comprising a reaction vessel 14. The reaction vessel 14 may comprise at least one feedstock inlet 15 (e.g., a first feedstock inlet and second feedstock inlet) in fluid connection with the reaction vessel 14; at least one catalyst feed inlet 16 in fluid connection with the reaction vessel 14; at least one reaction zone 17; a stripping zone 18 in fluid connection with the reaction zone 17; and at least one stripped catalyst outlet 19 in fluid connection with the reaction vessel 14. Additionally or alternatively, the stripping zone 18 may comprise a multiphase separator 1 as described above.

Additionally or alternatively, the stripping zone 18 may generally be positioned in a bottom portion of the reaction vessel 14 below the reaction zone 17. The at least one inlet chamber 2 (in a multiphase separator 1 as described above) may be adjacent to an edge of the reaction vessel 14.

Additionally or alternatively, the at least one moving bed reactor unit 13 may comprise multiple moving bed reactor units arranged in series and/or parallel. In particular, the multiple moving bed reactors are arranged in series.

V. Process Fluid Separation

In another embodiment, a process for separating a process fluid as described above from solid particles (e.g., catalyst) is provided. The process may comprise feeding the solid particles (e.g., catalyst) and the process fluid into at least one stripping chamber 4 as described above, e.g., having a top inlet 5 and a bottom outlet 6, defining perforations 7 therein as described above, and the top inlet 5 having a diameter greater than a diameter of the bottom outlet 6. In particular, the at least one stripping chamber 4 may be generally disposed between at least one inlet chamber 2 as described above and at least one collection chamber 8 as described above. The at least one stripping chamber 4 may generally have a (frusto)conical shape. Additionally, the at least one stripping chamber 4 may further comprise a stripping interface section 11 having a first angle (e.g., from about 5° to about 30°) and/or a guide section 12 having a second angle (e.g., from about 7° to about 45°), particularly where the first angle can be less than or equal to the second angle.

Additionally or alternatively, the process can further comprise introducing a stripping fluid as described above into the inlet chamber 2, wherein the stripping fluid can flow into the at least one stripping chamber 4 through the perforations 7, whereby at least a portion of the process fluid (e.g., liquid and/or gas product and/or unconverted feedstock) can be stripped from the solid particles (e.g., catalyst). Particularly, the stripping fluid can generally flow in a direction cross-current to a flow of the solid particles (e.g., catalyst). Additionally or alternatively, the stripping fluid may enter the at least one inlet chamber 2 at a flow rate, e.g. from about 1.0% to about 2000% a flow rate of the feedstock.

Additionally or alternatively, the separating may further comprise passing the process fluid (e.g., liquid and/or gas product and/or unconverted feedstock) from solid particles (e.g., catalyst) through the perforations 7 into the at least one collection chamber 8; and passing the stripped solid particles (e.g., catalyst) through the bottom outlet 6 of the at least one stripping chamber 4. Additionally or alternatively, the stripping fluid may pass through the perforations 7 into the at least one collection chamber 8. Additionally or alternatively, once passed into the at least one collection chamber 8, the stripping fluid and the process fluid (e.g., liquid and/or gas product and/or unconverted feedstock) may further exit the at least one collection chamber 8 via the at least one outlet 9.

VI. Further Embodiments

Embodiment 1. A multiphase separator for separating a process fluid (e.g., gaseous and/or liquid unreacted feed and/or product) from a catalyst comprising: at least one inlet chamber comprising at least one inlet for introducing a stripping fluid; at least one stripping chamber having a top inlet and a bottom outlet, wherein the at least one stripping chamber defines perforations therein, and wherein the top inlet has a diameter greater than the bottom outlet diameter;

at least one collection chamber comprising at least one outlet; wherein the at least one stripping chamber is generally disposed between the at least one inlet chamber and the at least one collection chamber and at least a portion of the perforations are in fluid communication with the at least one inlet chamber and the at least one collection chamber such that the stripping fluid enters the at least one inlet chamber and flows through the perforations into the at least one stripping chamber and into the at least one collection chamber; and at least one wall (e.g., including multiple walls) disposed on at least a portion of an exterior surface of the at least one stripping chamber, wherein the at least one wall guides the stripping fluid into the perforations of the at least one stripping chamber and prevents the stripping fluid from flowing directly into the at least one collection chamber.

Embodiment 2. The multiphase separator of embodiment 1, wherein the perforations have a substantially circular cross-section with a diameter of about 0.015 inches to about 0.063 inches and/or an open area of the perforations define about 20% to about 50% of the surface area of the at least one stripping chamber.

Embodiment 3. The multiphase separator of embodiment 1 or 2, wherein the at least one stripping chamber generally has a (frusto)conical shape.

Embodiment 4 The multiphase separator of any one of the previous embodiments, wherein the at least one stripping chamber comprises a stripping interface section having a first angle (e.g., from about 5° to about 30°, from about 5° to about 10°, or from about 7° to about 8°) and/or a guide section having a second angle (e.g., from about 7° to about 45°, from about 25° to about 35°, or from about 30° to about 35°), particularly where the first angle is less than or equal to the second angle.

Embodiment 5. The multiphase separator of any one of the previous embodiments, wherein the stripping fluid generally flows in a direction cross-current to a direction of flow of the catalyst.

Embodiment 6. The multiphase separator of any one of the previous embodiments, wherein the stripping fluid enters the at least one inlet chamber at a flow rate (e.g., about 1.0% to about 2000% of a flow rate of a feedstock) capable of causing: (i) flow of the stripping fluid through the perforations of the at least one stripping chamber; (ii) stripping of at least a portion of the process fluid from the catalyst in the at least one stripping chamber; and (iii) flow of the stripped process fluid and the stripping fluid into the at least one collection chamber.

Embodiment 7. The multiphase separator of any one of the previous embodiments, wherein the stripping fluid enters the at least one inlet chamber at a pressure of about 15 psig to about 1500 psig.

Embodiment 8. The multiphase separator of any one of the previous embodiments, wherein the at least one stripping chamber includes at least a first stripping chamber and a second stripping chamber, and wherein the at least one wall is generally disposed between the first stripping chamber and the second stripping chamber.

Embodiment 9. The multiphase separator of any one of the previous embodiments, wherein the at least one stripping chamber includes multiple stripping chambers and/or the multiple stripping chambers are generally disposed concentrically around the at least one collection chamber.

Embodiment 10. A multiphase separator for separating a process fluid from a catalyst comprising: (i) at least one inlet chamber comprising at least one inlet for introducing a stripping fluid; (ii) at least one stripping chamber comprising: a stripping interface section having a first angle, wherein the first angle is about 5° to about 10°; a guide section having a second angle, wherein the second angle is about 25° to about 35°; a top inlet and a bottom outlet, wherein the top inlet has a diameter greater than the bottom outlet diameter; and wherein the at least one stripping chamber defines perforations therein; (iii) at least one collection chamber comprising at least one outlet; wherein the at least one stripping chamber is generally disposed between the at least one inlet chamber and the at least one collection chamber and at least a portion of the perforations are in fluid communication with the at least one inlet chamber and the at least one collection chamber such that the stripping fluid enters the at least one inlet chamber and flows through the perforations into the at least one stripping chamber and into the at least one collection chamber; and (iv) at least one wall disposed on at least a portion of an exterior surface of the at least one stripping chamber, wherein the at least one wall guides the stripping fluid into the perforations of the at least one stripping chamber and prevents the stripping fluid from flowing directly into the at least one collection chamber.

Embodiment 11. A reaction system for converting a feedstock to a hydrocarbon product comprising at least one moving bed reactor unit comprising: a reaction vessel comprising at least one feedstock inlet in fluid connection with the reaction vessel; at least one catalyst feed inlet in fluid connection with the reaction vessel; at least one reaction zone; a stripping zone in fluid connection with the reaction zone, wherein the stripping zone comprises a multiphase separator of any one of the previous embodiments; and at least one stripped catalyst outlet in fluid connection with the reaction vessel.

Embodiment 12. The reaction system of embodiment 11 having one or more of the following: (i) the stripping zone is generally positioned in a bottom portion of the reaction vessel; (ii) the at least one inlet chamber is adjacent to an edge of the reaction vessel; (iii) the at least one moving bed reactor unit comprises multiple moving bed reactor units arranged in series and/or parallel; and (iv) the at least one feedstock inlet comprises a first feedstock inlet and a second feedstock inlet.

Embodiment 13. A process for converting a feedstock to a hydrocarbon product comprising: feeding the feedstock and a catalyst to a reaction zone of at least one moving bed reactor, wherein the feedstock and the catalyst travel through the at least one moving bed reactor under conditions to produce a three-phase mixture comprising converted hydrocarbon product (e.g., $C_2$-$C_{25}$ hydrocarbons), unconverted feedstock, and spent catalyst; passing the three-phase mixture to a stripping zone in the at least one moving bed reactor; and separating the three-phase mixture in the stripping zone, wherein the separating comprises: collecting the three-phase mixture in at least one stripping chamber having a top inlet and a bottom outlet, wherein the at least one stripping chamber defines perforations therein and the top inlet has a diameter greater than a diameter of the bottom outlet, and wherein the at least one stripping chamber is generally disposed between at least one inlet chamber and at least one collection chamber; introducing a stripping fluid into the at least one inlet chamber, wherein the stripping fluid flows into the at least one stripping chamber through the perforations whereby at least a portion of the converted hydrocarbon product (e.g., $C_2$-$C_{25}$ hydrocarbons) and optionally, the unconverted feedstock are stripped from the spent catalyst; passing at least a portion of the converted hydrocarbon product (e.g., $C_2$-$C_{25}$ hydrocarbons) and optionally, the unconverted feedstock stripped from the spent catalyst through the perforations into the at least one collection chamber; and passing the stripped catalyst through the bottom outlet of the at least one stripping chamber.

Embodiment 14. A process for separating a process fluid (e.g., gaseous and/or liquid unreacted feedstock and/or product) from a catalyst comprising: feeding the catalyst and the process fluid in a three-phase mixture into at least one stripping chamber having a top inlet and a bottom outlet, wherein the at least one stripping chamber defines perforations therein and the top inlet has a diameter greater than the bottom outlet diameter, and wherein the at least one stripping chamber is generally disposed between at least one inlet chamber and at least one collection chamber; introducing a stripping fluid into the inlet chamber, wherein the stripping fluid flows into the at least one stripping chamber through the perforations whereby at least a portion of the process fluid is stripped from the catalyst; passing at least a portion of the process fluid stripped from the spent catalyst through the perforations into the at least one collection chamber; and passing the stripped catalyst through the bottom outlet of the at least one stripping chamber.

Embodiment 15. The process of embodiment 13 or 14, wherein the at least one stripping chamber generally has a (frusto)conical shape.

Embodiment 16. The process of embodiment 13, 14 or 15, wherein the at least one stripping chamber comprises a stripping interface section having a first angle (e.g., about 5° to about 30°, about 5° to about 10°, or about 7° to about 8°) and/or a guide section having a second angle (e.g., about 7° to about 45°, about 25° to about 35°, or about 30° to about 35°), particularly where the first angle is less than or equal to the second angle.

Embodiment 17. The process of embodiment 13, 14, 15 or 16, wherein the stripping fluid generally flows in a direction cross-current to a flow of the spent catalyst.

Embodiment 18. The process of embodiment 13, 15, 16 or 17, wherein a temperature in the reaction zone is about 200° C. to about 500° C. and/or a pressure in the reaction zone is about 15 psig to about 1500 psig.

Embodiment 19. The process of embodiment 13, 14 15, 16, 17 or 18, wherein the stripping fluid enters the at least one inlet chamber at a flow rate of about ~1.0% to ~2000% a flow rate of the feedstock (e.g., into the at least one moving bed reactor).

Embodiment 20. The process of embodiment 13, 14 15, 16, 17, 18 or 19, wherein the catalyst comprises a zeolite (e.g., ZSM-5, ZSM-48, ZSM-23, ZSM-12, ZSM-57, and/or MCM-22), an ALPO, a SAPO or a combination thereof.

Embodiment 21. The process of embodiment 13, 15, 16, 17, 18, 19 or 20, wherein the feedstock comprise an oxygenate (e.g., a $C_1$-$C_4$ mono-alcohols, a di-alcohol, a polyol and/or dimethyl ether) and/or an olefin (e.g., a $C_{2+}$ olefin).

Embodiment 22. The process of embodiment 13, 15, 16, 17, 18, 19, 20 or 21, wherein the unconverted feedstock is in a single phase or a mixed phase and/or the converted hydrocarbon product is in a single phase or a mixed phase.

EXAMPLES

The following examples are merely illustrative, and are not meant to unduly limit this disclosure in any way.

Example 1

Stripping Efficiency

A cold flow apparatus was devised to determine the stripping efficiency of the multiphase separator described above. The apparatus consisted of a cylindrical vessel, a stripping chamber at the bottom of the vessel with the inlet and outlet chambers isolated with a wall disposed on the exterior surface of the stripping chamber, and a standpipe at the bottom of the stripping chamber for the removal of the spent particles from the vessel. Nitrogen was used as the stripping gas and introduced into the inlet chamber. The collection chamber had an outlet line for the removal of the stripped fluid from the vessel. The schematic of the stripping chamber is similar to the one shown in FIG. 1. The particles were spherical beads with ~1/16" ID and were pre-soaked with a hydrocarbon liquid before being charged to the column. The bulk density of the hydrocarbon-soaked particles was measured to be about 62% higher than that of the dry particles. The cold flow testing focused on the removal of the liquid from the interstices of the particles. Nitrogen as process gas (vapor) and a liquid hydrocarbon (liquid) were fed at the top of the column as surrogate for main process fluid. In a reactive system, however, the liquid may be formed in the reactor vessel. The flow of the particles was controlled at the bottom of the standpipe using a calibrated L-valve. The liquid recovered from the outlet chamber was collected in a liquid recovery tank, and the discharged solid particles from the outlet of the L-valve were collected in a solid recovery tank.

During the cold flow testing, one objective was to determine the relationship between the stripping gas flow rates and the stripping efficiency. The stripping efficiency, $\eta$, is defined as the ratio of the amount of liquid recovered from the stripping chamber in the liquid recovery tank, $m_{L,Recovered}$, to the total amount of liquid recovered, $m_{L,Total}$, which is the sum of the liquid recovered from the stripping section and in the solid recovery tank at the bottom of the L-valve, $m_{LS,Recovered}$, expressed as:

$$\eta = \frac{m_{L,Recovered}}{m_{L,Total}} \times 100 = \frac{m_{L,Recovered}}{m_{L,Recovered} + m_{LS,Recovered}} \times 100$$

Figure 5:
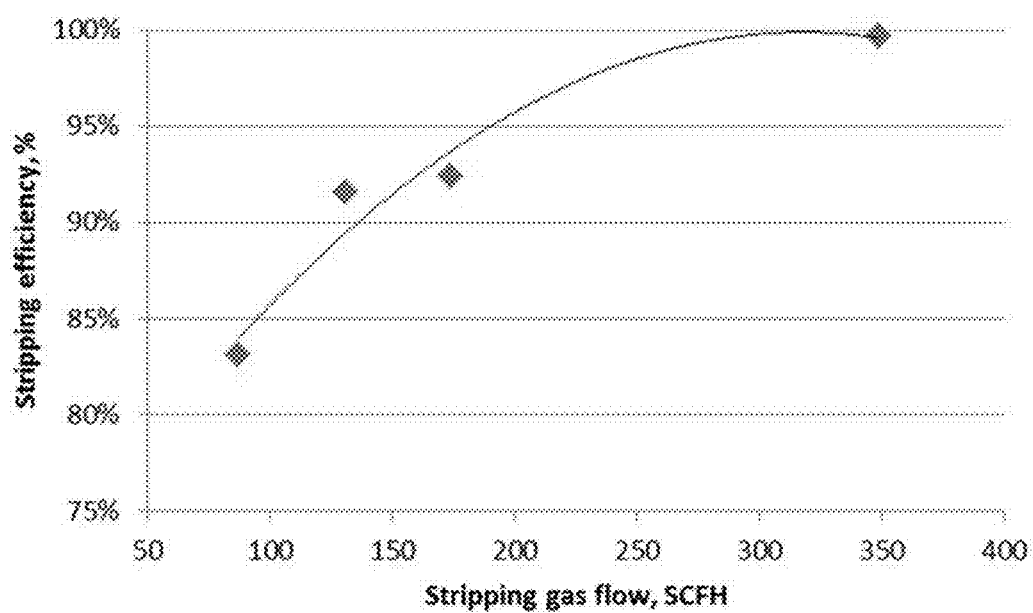
FIG. 5 illustrates effect of cross-current stripping gas flow rates on stripping efficiency.

In FIG. 5, the effect of the cross-current stripping gas flow rates on the stripping efficiency is shown. In this figure all the data were obtained with ~2 scfh vapor flow, ~1.1 g/s liquid feed, and stationary solid. While varying the stripping gas flow rates, the liquid flow rate and vapor flow rate were kept constant. As shown in FIG. 5, at about 300 scfh, the stripping efficiency becomes ~100%, meaning all the liquids in the interstices of the particles were removed. The relationship between the stripping flow rate and efficiency is also well defined and can be deduced that, for a ~90% removal efficiency, about 130-140 scfh is required. This is significant since it represents almost half the flow rate required for a total removal and hence can significantly reduce the flow dilution in the system.

Figure 6:
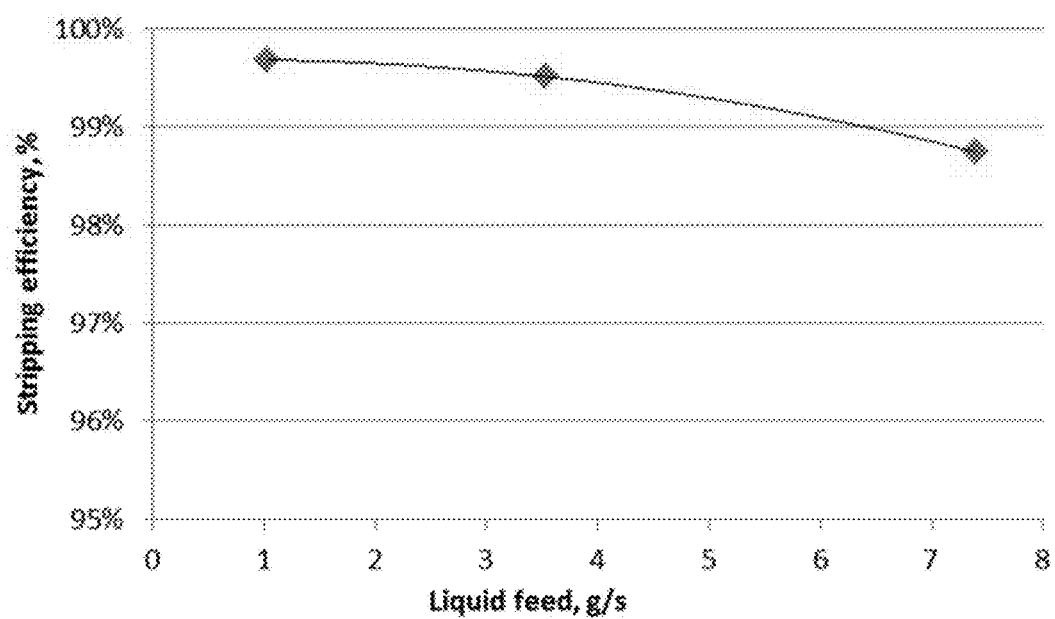
FIG. 6 illustrates effect of flow rate of feed on cross-current stripping efficiency.

As shown in FIG. 6, the liquid injection rate was increased to ~7.4 g/s while maintaining the maximum stripping flow rates of ~349 scfh. FIG. 6 shows that a ~7 fold increase in liquid rate can result in less than ~1% decrease in the stripping efficiency.

Figure 7:
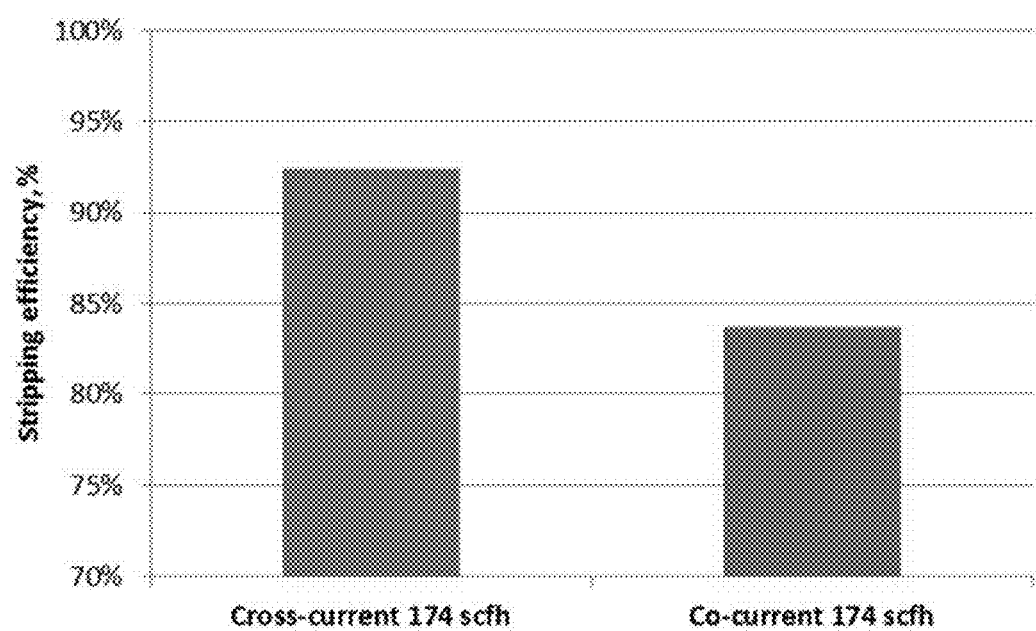
FIG. 7 illustrates stripping efficiency for cross-current and co-current flow of a stripping fluid.

Another test was to determine the effect of a co-current mode of operation, with the cross-current stripping gas from the previous stage (i-1) being introduced along with the reactor fluid to the top of the next stage (i). This is the case where the stripping gas cannot be purged in between stages. The effect of this additional flow on the flow behavior of the vapor and liquid should be determined before re-introducing an equal amount of the stripping gas at the bottom of stage (i). Depending on which path the vapor and liquid choose to travel at the bottom of stage (i), the amount of stripping gas needed in stage (i) can be determined. For comparison purposes with the cross-current mode, a flow of ~174 scfh was selected and introduced at the top along with ~1.1 g/s of liquid. A very small amount of the cross-current gas (~7 scfh) was introduced directly into the inlet chamber of the stripping section to prevent the liquid from entering the inlet chamber. FIG. 7 shows the comparison between the cross- and co-current stripping mode at ~174 scfh. As shown in FIG. 7, the efficiency dropped from about 92% to about 84% when switching the operation mode from cross- to co-current, thus indicating that the stripping gas flow rate requirements in subsequent stages of a moving bed can be significantly reduced to yield an acceptable stripping efficiency.

The invention claimed is:

1. A process for converting a feedstock to a hydrocarbon product comprising:
    providing at least one moving bed reactor comprising a reaction zone and a stripping zone;
    feeding the feedstock and a catalyst through at least one inlet located at the top of the moving bed reactor to the reaction zone, wherein the feedstock and the catalyst travel in a downflow motion through the reaction zone under conditions to produce a three-phase mixture comprising converted hydrocarbon product, unconverted feedstock and spent catalyst;
    passing the three-phase mixture to the stripping zone located below the reaction zone, wherein the stripping zone comprises
    at least one stripping chamber having a top inlet and a bottom catalyst outlet, wherein the at least one stripping chamber has perforations defined therein and the top inlet has a diameter greater than a diameter of the bottom catalyst outlet, and wherein the a least one stripping chamber is disposed between an inlet for a stripping fluid and at least one collection chamber;
    separating the three-phase mixture in the stripping zone by introducing the stripping fluid through the inlet into the, wherein the stripping fluid flows into the at least one stripping chamber through the perforations whereby at least a portion of the converted hydrocarbon product is stripped from the spent catalyst;
    passing at least a portion of the converted hydrocarbon product and at least a portion of the unconverted feedstock stripped from the spent catalyst through the perforations into a fluid outlet located at the bottom of the stripping zone to the at least one collection chamber; and
    passing the stripped catalyst through the bottom catalyst outlet of the stripping chamber.

2. The process of claim 1, wherein the at least one stripping chamber has a frustoconical shape.

3. The process of claim 1, wherein the at least one stripping chamber comprises a stripping interface section having a first angle.

4. The process of claim 2, wherein the at least one stripping chamber further comprises a guide section having a second angle.

5. The process of claim 3, wherein the first angle is less than or equal to the second angle.

6. The process of claim 2, wherein the first angle is about 5° to about 30°.

7. The process of claim 3, wherein the second angle is about 7° to about 45°.

8. The process of claim 1, wherein the stripping fluids flows in a direction cross-current to a flow of the spent catalyst.

9. The process of claim 1, wherein a temperature in the reaction zone is about 200° C. to about 500° C.

10. The process of claim 1, wherein a pressure in the reaction zone is about 15 psig to about 1500 psig.

11. The process of claim 1, wherein the stripping fluid flows into the stripping chamber at a flow rate of about 1% to about 2000% of a flow rate of the feedstock into the reaction zone.

12. The process of claim 1, wherein the catalyst comprises a zeolite, an ALPO, a SAPO or a combination thereof.

13. The process of claim 11, wherein the zeolite comprises ZSM-5, ZSM-48, ZSM-23, ZSM-12, ZSM-57 and/or MCM-22.

14. The process of claim 1, wherein the feedstock comprise an oxygenate and/or an olefin.

15. The process of claim 14, wherein the oxygenate comprises a $C_1$-$C_4$ mono-alcohol, a di-alcohol, a polyol and/or dimethyl ether.

16. The process of claim 14, wherein the olefin comprises a $C_{2+}$ olefin.

17. The process of claim 1, wherein the converted hydrocarbon product comprises $C_2$-$C_{25}$ hydrocarbons.

18. The process of claim 1, wherein the unconverted feedstock is in a single phase or a mixed phase.

19. The process of claim 1, wherein the converted hydrocarbon product is in a single phase or a mixed phase.

* * * * *